(12) United States Patent
Howe

(10) Patent No.: US 10,463,455 B2
(45) Date of Patent: Nov. 5, 2019

(54) FORMED DENTURE AND METHOD OF MAKING SAME

(71) Applicant: Global Dental Science, LLC, Scottsdale, AZ (US)

(72) Inventor: Devon O. Howe, Saratoga Springs, NY (US)

(73) Assignee: GLOBAL DENTAL SCIENCE, LLC, Scottsdale, AZ (US)

( * ) Notice: Subject to any disclaimer, the term of this patent is extended or adjusted under 35 U.S.C. 154(b) by 330 days.

(21) Appl. No.: 15/493,029

(22) Filed: Apr. 20, 2017

(65) Prior Publication Data
US 2018/0042705 A1 Feb. 15, 2018

Related U.S. Application Data

(60) Provisional application No. 62/374,471, filed on Aug. 12, 2016.

(51) Int. Cl.
| | |
|---|---|
| A61C 13/34 | (2006.01) |
| A61C 13/107 | (2006.01) |
| A61C 13/01 | (2006.01) |
| A61C 13/00 | (2006.01) |
| A61C 13/10 | (2006.01) |

(52) U.S. Cl.
CPC ...... *A61C 13/0001* (2013.01); *A61C 13/0004* (2013.01); *A61C 13/0019* (2013.01); *A61C 13/0022* (2013.01); *A61C 13/04* (2013.01); *A61C 13/10* (2013.01); *A61C 13/1003* (2013.01); *A61C 13/34* (2013.01)

(58) Field of Classification Search
CPC ....... A61C 5/77; A61C 13/01; A61C 13/0006; A61C 13/0019; A61C 13/0004
See application file for complete search history.

(56) References Cited

U.S. PATENT DOCUMENTS

| | | | |
|---|---|---|---|
| 8,641,938 B2 | 2/2014 | Howe | |
| 2013/0101962 A1* | 4/2013 | Howe | A61C 9/0053 433/191 |
| 2018/0055611 A1* | 3/2018 | Sun | A61C 13/0004 |

OTHER PUBLICATIONS

N. Savic, PalaDigital.com, "My Digital Denture," Supplement to Inside Dental Technology magazine, AEGIS Communications, Mar. 2017. accessed at http://editiondigital.net/publication/?i=385198#{"issue_id":385198,"page":0}. EFS file name: 20170526_15-493029_IDS_NPL_Cite1.

(Continued)

*Primary Examiner* — Jacob T Minskey
*Assistant Examiner* — Cedrick S Williams
(74) *Attorney, Agent, or Firm* — Derrick W. Harvey; Harvey Law, P.C.

(57) ABSTRACT

A method of fabricating a denture, comprising milling a preliminary try-in denture from denture material comprising a layer of denture base material contiguous with a layer of denture tooth material. Denture base material is removed from the block to form a first part of the, labial, buccal, gingival, and flange regions of the denture base to form a preliminary denture. A preliminary mold is created from this preliminary denture. The preliminary denture is then further modified with deformable waxes in gingival and anterior tooth recesses to form a preliminary try-in denture, which is fitted to a patient and adjusted to optimal dimensions. The adjusted try-in denture is then reproduced by further molding methods, producing the final denture.

21 Claims, 14 Drawing Sheets

(56) References Cited

OTHER PUBLICATIONS

Baltic Denture System product information printed on May 16, 2017 from Baltic Denture System website at http://www.baltic-denture-system.com/. Posting date unknown. EFS file name: 20170526_15-493029_IDS_NPL_Cite2.

AvaDent product information printed on May 16, 2017 from AvaDent website at http://www.avadent.com/presentation_video/workflow/. Posting date unknown. EFS file name: 20170526_15-493029_IDS_NPL_Cite3.

Morales et al., "A Digital Spin on Traditional Dentures," Chairside Magazine, vol. 11, Issue 4, Glidewell Laboratories, Mar. 27, 2017. EFS file name: 20170526_15-493029_IDS_NPL_Cite4.

* cited by examiner

FORMED DENTURE AND METHOD OF MAKING SAME

CROSS-REFERENCE TO RELATED PATENT APPLICATIONS

This application claims priority to U.S. Patent Application No. 62/374,471, filed on Aug. 12, 2016, the disclosure of which is incorporated herein by reference.

BACKGROUND

Technical Field

Dental prostheses and apparatus and methods of manufacturing them. In particular, computer-implemented methods of manufacturing dental prostheses, a computer-aided system for manufacturing dental prostheses, and dental prostheses made by the system and method.

Description of Related Art

Heretofore, the manufacturing of dental prostheses has been a highly labor intensive process requiring multiple fittings to a patient in need of them, and many steps that must be performed at the hands of skilled artisans. The dental prostheses may be a complete upper and/or lower set of prosthetic teeth and their mountings, i.e., complete dentures; or partial dentures, crowns, bridges, and the like.

Advances have been made in Computer Aided Design and Computer Aided Manufacturing (CAD/CAM) of dental prostheses. For example, a CAD/CAM based system has been developed to make crowns in a dental office by milling a ceramic blank. Additionally, most other CAD/CAM systems that have been introduced to-date have been developed for "fixed" restorative dentistry, such as crowns, bridges, inlays, etc., i.e., devices that are cemented (or bonded) onto natural dentition.

The use of CAD/CAM in restorative dentistry has the potential of reducing processing errors that are common among conventional techniques. By way of illustration, the following are the steps currently practiced without CAD/CAM in many "dental laboratories" for the fabrication of a conventional fixed dental prosthetic known as a crown:

1) A dentist prepares the tooth (or teeth) of a patient to be fitted with a fixed prosthetic by removing tooth structure that is decayed, or to allow for space needed by the prosthetic device.
2) An accurate impression of the patient's existing gums and prepared teeth is made by the dentist at the dentist's office.
3) Gypsum material is poured into the impression to form a model (replica) of the dentition to be treated.
4) Wax is typically used to make a coping (thin metal substructure) on the model.
5) Using the "lost wax technique," the wax is invested (covered) by a phosphate investment material and then it is heated to burn out (remove) the wax, leaving a void in its place.
6) Metal is cast into the void created by the loss of wax to create a metal coping.
7) The metal coping is finished with grinding stones, and typically heat-treated.
8) Porcelain powder dispersed in water is painted onto the metal coping.
9) The porcelain is fired in a furnace to sinter it into a continuous hard coating, resulting in the finished crown.

It can be seen that in the above highly labor-intensive process, each of these steps introduces a potential for a processing error. Even the slightest error, such as the investment being too cool, or the powder/water ratio of the investment being incorrect, may cause the crown to fit too tightly in the patient's mouth, resulting in improper occlusion (upper and lower teeth engagement). The crown may thus have to be scrapped or reworked through at least one iteration of additional process steps at considerable cost to the patient, dentist, and/or manufacturing lab.

Currently, CAD/CAM for "fixed" restorative dentistry has evolved to the point where a digital impression can now be made in the dentist's office and the entire process can be computer implemented. However, certain shortcomings still remain in fixed restorative dentistry as presently practiced. For example, subtle irregularities often found in anterior (front) teeth are difficult to replicate using CAD/CAM processes. Manual methods of making anterior fixed prosthetics enable unlimited aesthetic options, only limited by the creativity of the artisan (dental laboratory technician). Some CAD/CAM techniques involve the use of milling a monolithic block of ceramic that does not deliver optimal aesthetics (example: too opaque), especially for anterior applications. For example, most natural teeth exhibit translucency and subtle color variations. A common solution for this problem is for a dental technician to apply a stain and/or glaze of porcelain over the prosthetic made by CAD/CAM. However, this manual step may defeat the primary benefit of CAD/CAM: precise dimensional accuracy.

With regard to the manufacturing of removable dental prosthetics, such as complete dentures and partial dentures, implementation of CAD/CAM has begun to occur. A key technology that is used in some CAD/CAM denture manufacturing applications is "fused deposition modeling" (FDM). In FDM, a computer-controlled machine builds a three dimensional part by ejecting microscopic droplets of material while repeatedly traversing in an x-y plane, building the part layer-by layer. In a sense, the machine "ink-jet prints" each layer, and hence FDM is also referred to as "3D printing." The physical model is built according to a three-dimensional virtual model that is prepared using CAD software and uploaded to the FDM machine.

CAD/CAM systems have recently been developed and used for the fabrication of partial denture frameworks. One such system uses a "haptic" device, which mimics a waxing tool that is familiar to dental technicians. However, this system generates only a CAD replica in plastic (made by a 3D printer), which requires subsequent extensive processing to obtain a metal partial denture framework. Hence there are still many error-prone steps after the CAD replica is made that can result in a poorly-fitting partial denture framework.

There have been some efforts by major manufacturers of dental materials to make a system to produce a complete (full) denture by 3D printing. The system includes a three-dimensional scanner for scanning an impression, software for creating a three-dimensional model of the denture, and the fused deposition modeling equipment for "printing" the denture. However, the materials available to use in three-dimensional printers are neither as dense nor cross-linked like a normal plastic artificial tooth. Hence a problem remains with the resulting dentures because the denture teeth that are made with available 3D printing plastic materials are not sufficiently wear-resistant.

An alternative approach to denture fabrication is to mill blocks of polymerized plastic to make a complete denture. This process involves milling a block of pink methacrylate material as the denture base (including the gingiva surrounding the teeth). The teeth are then milled from a single piece of PMMA material that is shaded from semi-translucent to more opaque. The variation of opacity allows the teeth to be milled so that the incisal edges of the teeth are more translucent so that they appear like natural human dentition. The pink denture base and the milled teeth are cemented together. This technique is useful to make an immediate (after tooth-extraction) denture for temporary use. The reason that this method cannot be used for long-term dentures is that the artificial teeth must be "glued" into position, thus this interface between the teeth and the base is susceptible to bacteria growth and debonding of the teeth from the base over time due to the oral fluids which may degrade the bonding material. In addition, the denture appliance must be mounted in an articulator and the occlusion then checked. This extra labor is required because the exact position of the teeth cannot be assured in the manual "gluing" procedure.

In summary, there remains a need for a method and apparatus for fabricating a highly durable denture at low cost, in a minimal number of steps, with reduced labor costs with minimal trial fittings to the patient. A denture made by any such method and apparatus must be made with sufficient precision so as to fit the patient properly, and have teeth that are firmly retained, wear resistant, and aesthetically pleasing.

SUMMARY

The method of the present disclosure, and a denture fabricated thereby, meet this need. In general, the method of denture fabrication entails the use of making a "preliminary try-in denture" out of synthetic denture material that is provided with two distinct color zones. One color zone has the appearance of natural teeth and the other color zone has the appearance of natural gum tissue. The preliminary try-in denture (which becomes part of or all of the resulting final denture) is milled so that the artificial teeth are milled from the tooth-colored zone and most of the denture base is milled from the natural gum tissue colored zone.

When the milling process of this first denture is complete, a primary mold is made of the tooth side of the denture to form an "index." After the primary mold is made, the first denture goes back into the mill for a second milling step.

In the second milling step, where the tooth-colored zone overlaps into the area of the denture that would normally be tissue-colored, this area may be "cut-back," i.e., removed by milling (or another suitable subtractive process). In certain embodiments, the removal of material may result in recesses, which may later be filled with gum colored material. The tooth-colored zones that overlap into the area of the denture that would normally be tissue-colored may be in the gingival portions, labial/buccal areas of the denture, and also the lingual/palatal regions of the denture. Accordingly, gingival, labial/buccal and lingual/palatal recesses may be formed, and subsequently back-filled with gum colored material.

Additionally, in this second milling step of the maxillary or mandibular denture, it may be made without some of the anterior teeth, e.g., without six teeth (two central incisors, two laterals, two canines); or four teeth (centrals, laterals, canines); or two (centrals) teeth. In the area where the anterior teeth are missing, this denture base material may be milled to the geometry of the gums. An additional amount (typically 1 to 3 millimeters) of denture base material may be further removed to provide anterior tooth sockets for receiving a temporary wax.

Once the second milling step is completed, anterior denture teeth that are not present are placed into the primary mold in corresponding anterior tooth cavities. The second-milled denture is then placed into the preliminary mold. Melted liquid wax is injected into anterior tooth chambers formed between the preliminary second milled denture and the bases of the anterior teeth that were placed into the tooth cavities of the preliminary mold, and also into gingival chambers formed between the gingival recesses and gingival cavities in the preliminary mold. Wax fills any tooth-colored zones that overlap into the area of the denture that would normally be tissue-colored, and was milled out in the second milling step. The wax cools and solidifies, thereby adjustably joining the anterior teeth to the second-milled denture, to form a "complete try-in denture." The complete try-in denture is removed from the preliminary mold. This complete try-in denture is thus comprised of three materials: the milled synthetic denture base material, denture teeth of a synthetic denture tooth material, and a solid wax. The wax is molded around and beneath the anterior denture teeth and may also mask any tooth-colored material in the gingival regions that would normally be tissue-colored, in particular, those regions that are visible to a wearer of the denture (looking in a mirror), or an observer of the wearer.

The complete try-in denture is fitted to the patient for the purposes of evaluating fit, function and aesthetics of the denture. Additionally, the wax that is disposed between the denture base material and the anterior teeth is a solid material that has a low yield point and is subject to deformation when a threshold stress is applied. In that manner, the positions of the anterior teeth can be adjusted by the dental practitioner during a try-in of the complete try-in denture on the patient. The dental practitioner may make adjustments to the position of the anterior teeth by gently forcing the teeth upward or downward or anteriorly or posteriorly, deforming the wax as needed to make the adjustments. (In some cases, the wax may be softened prior to movement by the application of heat).

Additionally, the posterior teeth of the complete try-in denture may be adjusted for optimal occlusion by using articulating paper and a bur to locate "high spots" and then grinding each "high-spot" down in progressive steps. A jaw recording device, such as a Gothic Arch tracing system (e.g., a Massad Jaw Recorder) may be used to make this process efficient and accurate. The borders of the denture are evaluated for fit and adjusted as required. The patient may also comment on areas that feel tight or cause pressure on their dental ridge, and those areas can be adjusted, such as by grinding with a bur. In some cases, a pressure indicating paste may be used to determine where interferences are present, and then those interferences are adjusted. The optimally adjusted try-in denture is then removed from the patient, and a "final denture mold" of it is made. The adjusted try-in denture is removed from the final denture mold, and the anterior teeth and try-in gingival and anterior tooth waxes are removed (often using hot water and steam), resulting in a "semi-complete" denture.

The anterior teeth are placed in the corresponding anterior tooth cavities of the final denture mold, and the semi-complete denture is also placed into the final denture mold. The gingival anterior tooth and gingival chambers between the semi-complete denture and the final denture mold are filled or injected with denture base material that is tissue-colored to closely match the milled semi-complete denture in the area of the natural gum tissue color. The denture base material is cured (polymerized) and the anterior teeth are bonded to the semi-complete denture to form the "completed denture", which is then removed from the mold. Deburring and polishing may be performed as needed to produce the "final denture" for final fitting to and use by the patient.

In certain embodiments of fabrication of a denture according to the method, CADCAM design and milling of a denture base and posterior teeth, and the separate anterior teeth are used with CADCAM design and 3D-printing or milling of a first-milled denture for producing the initial molding and try-in denture formation steps. The method is advantageous in that it results in a better fitting and longer life denture that is completed in final form in less time than conventional denture fabrication methods. Additionally, the posterior teeth may be milled-away completely in the secondary milling step, and denture teeth can be substituted by placing the posterior teeth into the preliminary mold in the same steps as the anterior teeth, as described above. Additionally, for an "economy denture," the second milling step may be combined in the first milling step and the anterior teeth may be left in place; instead, only the tooth-colored material in areas that should be tissue-colored are "cutback." In this case, the first-milled denture becomes the try-in denture or the final denture. However, in such an embodiment, the teeth can only be reduced in size by grinding with a handpiece; the position of the teeth cannot be moved.

The above recited advantages, and other advantages, will be described in further detail subsequently in this disclosure.

In further summary, in accordance with the present disclosure, a method of fabricating a denture is provided. The denture is comprised of a denture base comprising a labial region, buccal regions, gingival regions, and flange regions, and anterior denture teeth and posterior denture teeth joined to the base. The method comprises, from a block of denture material comprising a layer of denture base material contiguous at an interface with a layer of denture tooth material, removing denture base material from the block to form the buccal, labial, and flange region of the denture base; removing denture base material from the block to form a first portion of the gingival regions of the denture base that are contiguous with the interface with the layer of denture tooth material; removing denture tooth material to form a second portion of the gingival regions of the denture base that were contiguous with the interface with the layer of denture base material prior to the removing denture base material form the first portion of the gingival regions; and removing denture tooth material to form the posterior denture teeth and anterior denture teeth, thereby forming this first-milled denture as a preliminary try-in denture including the posterior denture teeth, anterior denture teeth, and the denture base. The preliminary try-in denture is then encased in a mold forming material to form a preliminary mold from this first-milled denture.

The preliminary try-in/first-milled denture is removed from the mold. The resulting empty preliminary mold includes anterior tooth cavities, posterior tooth cavities, and a denture base cavity. The preliminary try-in/first-milled denture is then placed back into the mill and reindexed. Then selected teeth (preferably anterior teeth) are removed by the milling process. In certain embodiments, at least one pair of anterior teeth is removed by milling to form at least one pair of corresponding anterior tooth cavities. Additional recesses may also made to allow for denture base material to flow into chambers bounded by the anterior tooth sockets in subsequent steps performed in order to secure the denture teeth to the second-milled denture. Denture tooth material from the second portion of the gingival regions of the denture base is then removed to form gingival recesses proximate to base portions of the denture teeth.

In another embodiment, the first-milled denture can be made by alternative means, such as additive (3D printing) or other subtractive methods. This can be used to make the preliminary mold. In another embodiment, the first mold itself can be made by additive (3D printing) or other subtractive methods.

Anterior denture teeth are then disposed in at least one pair of anterior tooth cavities in the preliminary mold. The anterior denture teeth have the same respective dimensions as the anterior denture teeth of the first milled denture. Each anterior denture tooth is disposed in a correspondingly dimensioned anterior tooth cavity of the preliminary mold. The preliminary try-in/second-milled denture is then disposed in the mold cavity of the preliminary mold with the posterior teeth disposed in the posterior tooth cavities and the denture base disposed in the denture base cavity. A deformable solid wax is then disposed in the anterior tooth chambers bounded by the bases of the anterior denture teeth and the anterior tooth sockets, resulting in the formation of a complete try-in denture.

The complete try-in denture is removed from the preliminary mold and fitted to the mouth of a patient. The dental practitioner then modifies the complete try-in denture to adjust and optimize the fit thereof to the mouth of the patient, thereby forming an adjusted try-in denture. The adjusted try-in denture is removed from the mouth of the patient. A mold forming material is applied to the adjusted try-in denture to form a final mold of the denture comprising final anterior tooth cavities, final posterior tooth cavities, a final labial, buccal, and flange cavities, and a final gingival cavity.

The adjusted try-in denture is removed from the final mold, the anterior denture teeth are removed from the adjusted try-in denture, and the deformable solid wax material is removed from the adjusted try-in denture to form a semi-complete denture, which includes the gingival recesses and anterior tooth sockets. The anterior denture teeth are placed in corresponding final anterior tooth recesses in the final mold of the denture, and the semi-complete denture is placed in the final mold of the denture with the posterior denture teeth disposed in corresponding final posterior tooth cavities, and the labial, buccal, gingival, and flange regions disposed in respective final labial, buccal, gingival, and flange cavities. Anterior tooth chambers bounded by the anterior denture teeth and the anterior tooth sockets, and gingival chambers bounded by the gingival recesses and final gingival cavities of the final mold are filled with a final denture base material. This final denture base material is cured to form a completed denture. The final denture base material is formulated so that it blends in and is visually indistinguishable with the adjacent denture base material of the palatal (if present), labial, buccal, and flange regions of the completed denture. The completed denture is removed from the final mold. The denture base and the denture teeth may be polished to produce a finished denture.

In certain embodiments, forming the palatal region of the denture base (if present), the buccal, labial, gingival, and flange regions of the denture base, and the posterior denture teeth are performed by milling (or other subtractive methods) denture base material and denture tooth material from the block. As noted previously, the block of denture material comprises a layer of denture base material and a layer of denture tooth material.

The denture tooth material may be non-homogeneous, having a gradient of translucency from lowest translucency to highest translucency along a first axis, in which case the block may be oriented during forming the posterior denture teeth and first portions of the denture base palatal region (if present) and the flange outer region such that the posterior denture teeth are formed with lower translucency at bases of the teeth and higher translucency at outer extremities of the teeth. Additionally, the anterior denture teeth may also be formed from a non-homogeneous denture tooth material having a gradient of translucency from lowest translucency to highest translucency along a first axis, in which case the denture tooth material is oriented during forming the anterior denture teeth such that the anterior denture teeth are formed with lower translucency at bases of the teeth and higher translucency at outer extremities (incisal edges) of the teeth.

Forming the preliminary mold of the denture and the final mold of the denture may be performed by vacuum molding, or molding in silicone (moldable putty or liquid), colloid (agar), milling, or an additive manufacturing process. The molds may each include at least one sprue in fluid communication with the palatal recesses (if present) and the gingival recesses to enable filling them with the temporary denture base wax material, and then the final denture base material.

In certain embodiments, the final mold may be made by digitally scanning the adjusted temporary denture, and using the digital data to operate a CNC milling machine that fabricates the mold. Alternatively, the final mold may be made by an additive manufacturing process such as 3D printing. In other embodiments, the adjusted temporary denture may be encased in a mold material to form the final mold, such as by vacuum molding, or molding in silicone elastomer in putty (semi-solid) or liquid state. In another approach, the final mold may be made by embedding the temporary denture into silicone, hydro-colloid or other molding material.

The denture may be defined by a digital three-dimensional model. In such embodiments, the forming the posterior denture teeth and the portions of the denture base from the block of denture tooth material and the forming the anterior teeth from denture tooth material may be performed based upon data from the three-dimensional model. The digital three-dimensional model may be based upon three-dimensional data obtained from a digital scan of features of the mouth of a patient, or a model of the mouth of a patient, to whom the denture is to be fitted.

It is noted that dentures intended for fitting to a patient's lower teeth, i.e. lower dentures, do not include a palatal region. In contrast, in embodiments in which the denture is an upper denture having a palatal region, the method further comprises forming the palatal region in the completed denture. Accordingly, the Applicant's method to make such a denture is similar to the method recited above, but further includes the steps of forming the palatal region from the block of denture material, and forming a final palatal recess in the final mold.

In another embodiment, a denture may be fabricated from a first milling step performed on a block of denture material comprising a layer of denture base material and a layer of denture tooth material, with the denture base material being of a pink gum color, and the denture tooth material being white tooth colored material (and possibly having a translucency gradient), as described previously. Additionally, in the gingival portions proximate to the denture teeth that are formed of denture tooth material, those portions may be milled away to form gingival and lingual/palatal recesses. These recesses may subsequently be back-filled with gum colored denture base material to produce the final denture. Such a simple denture fabrication method is enabled by the use of the block of denture material comprising a layer of denture base material and a layer of denture tooth material as a starting block of material. The resulting denture is of low cost, and may be provided to a patient as an "economy denture" option.

In another embodiment of a low cost denture, but with some custom fitting to the patient, the denture may be first fabricated as a try-in denture from a block of denture material comprising a layer of denture base material and a layer of denture tooth material. The gingival recesses may be formed prior to a try-in fitting on the patient, or after the try-in fitting. In either case, the try-in denture is fitted to the patient, and the dental practitioner makes adjustments to the teeth or denture base with a bur, grinding small amounts of denture tooth or base material from the denture teeth to optimize their fit in the patient. Following the try-in adjustment by the practitioner, the gingival recesses are back-filled with gum colored denture base material to produce the final denture.

BRIEF DESCRIPTION OF THE DRAWINGS

The present disclosure will be provided with reference to the following drawings, in which like numerals refer to like elements, and in which.

Figure 1:
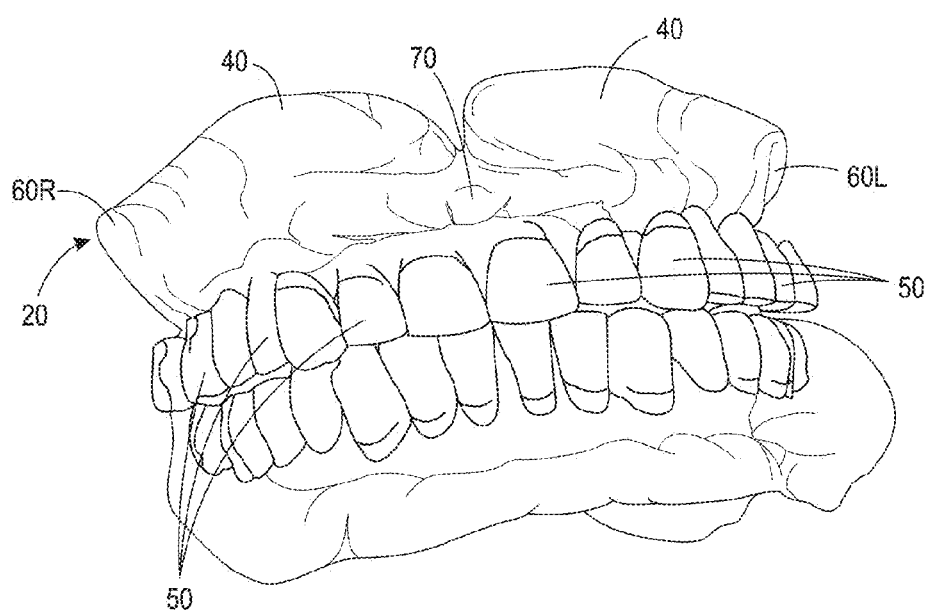
FIG. 1 is an exploded perspective illustration of upper denture teeth and an upper denture base that may comprise an upper denture, and lower denture teeth and a lower denture base that may comprise a lower denture.

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used throughout to designate identical elements. The drawings are to be considered exemplary, and are for purposes of illustration only. The dimensions, positions, order and relative sizes reflected in the drawings attached hereto may vary.

In the following disclosure, the methods of the present invention are described in the context of their use for fabrication of an upper denture, which includes a palatal region. However, they are not to be construed as being limited only to use in fabricating upper dentures. The methods are adaptable to fabrication of lower dentures as well as other dental prostheses. Additionally, the description may identify certain structures with the adjectives "top," "upper," "bottom," "lower," "left," "right," etc. These adjectives are provided in the context of use of the method in fabricating an upper denture, and in the context of the orientation of the drawings, which is arbitrary. The description is not to be construed as limiting the methods to use in a particular spatial orientation. Various steps of the methods may be performed in orientations other than those shown and described herein.

It is also to be understood that any connection references used herein (e.g., attached, coupled, connected, and joined) are to be construed broadly and may include intermediate members between a collection of elements and relative movement between elements unless otherwise indicated. As such, connection references do not necessarily imply that two elements are directly connected and in fixed relation to each other.

Turning now to FIG. 1, individual upper denture teeth and an upper denture base that may comprise an upper denture, and individual lower denture teeth and a lower denture base that may comprise a lower denture are depicted. The respective denture teeth and denture bases may be defined by individual digital three-dimensional models, or combined in "denture assembly" models. To produce the digital three-dimensional models using Computer Aided Design (CAD) software (such as Solid/Works®, ProEngineer®, 3Shape™, Dental Wings, Exocad® Sirona, or E4D, etc.), a dentist will first capture an impression of the dental arches, or use a digital scanner in communication with a computer to create a digital file of the dental arches. If using an impression, the impression may be scanned, or a model may be poured from the impression, and then the model is scanned. The digital data of the patient's mouth includes the impression or model and occlusal registration of the complete denture and opposing arch.

Subsequently, based upon the data of the patient's mouth, a dental laboratory technician or dentist may design the patient's denture virtually using CAD software. In one embodiment of the present method, at least two CAD software files are created: one being a three dimensional model of the majority of the denture base in combination with the denture teeth; and the other being a three dimensional model (or individual models) of the pink veneer layers of the visible gingival and palatal areas (or defined as potentially visible pink areas) when the denture is seated in the patient's mouth. In another embodiment, a single CAD software file is created and the junction between the pink gingiva and the denture teeth are delineated.

Figure 14A:
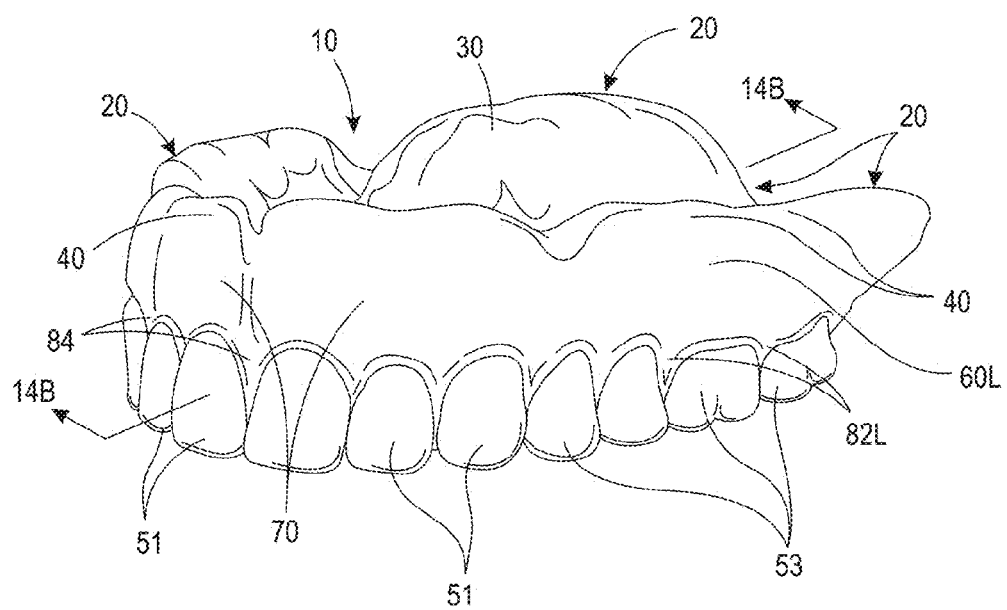
FIG. 14A is a perspective view of a finished denture made in accordance with the method.
Figure 14B:
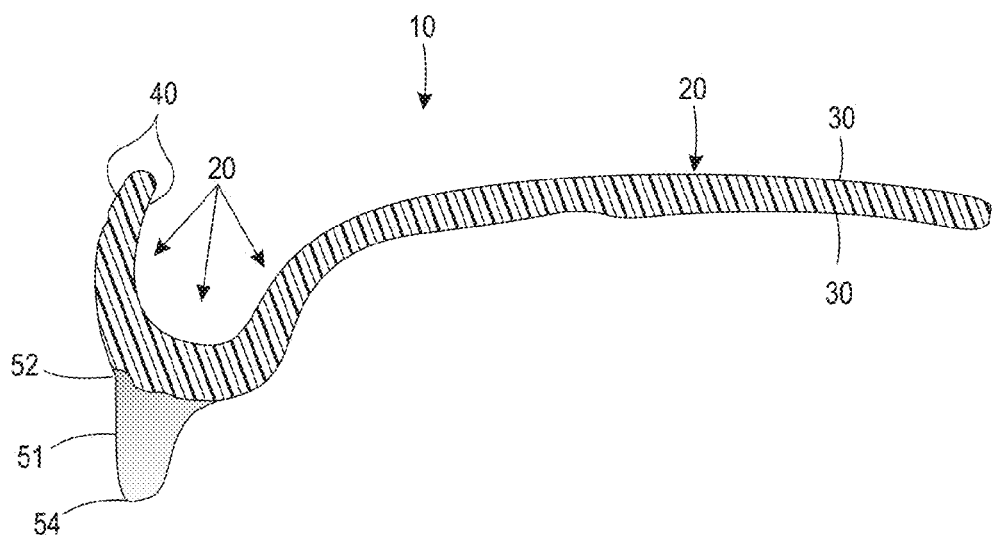
FIG. 14B is a cross-sectional view of the finished denture of FIG. 14A taken along the line 14B-14B of FIG. 14A.

FIG. 1 is an exploded perspective illustration of an upper denture comprised of upper denture teeth and an upper denture base, and a lower denture comprised of lower denture teeth and a lower denture base. Referring also to FIGS. 14A and 14B, which depict a finished upper denture 10, the upper denture 10 is comprised of upper denture base 20 comprising a palatal region 30, a flange region 40, buccal regions 60L and 60R, a labial region 70, and a plurality of teeth 50, including anterior teeth 51 and posterior teeth 53. When the denture 10 is fitted to the mouth of a user, the buccal regions 60L and 60R are in contact with the cheeks of the user, and the labial region 70 is in contact with the upper lip of the user. The flange 40 is formed as a contiguous ridge that extends along the upper portions of the buccal regions 60L, the labial region 70, and the buccal region 60R. Additionally, the upper denture base 20 includes gingival regions that are proximate to the denture teeth. Buccal gingival region 82L is proximate to the posterior teeth 53, and labial gingival region 84 is proximate to anterior teeth 51.

Figure 2A:
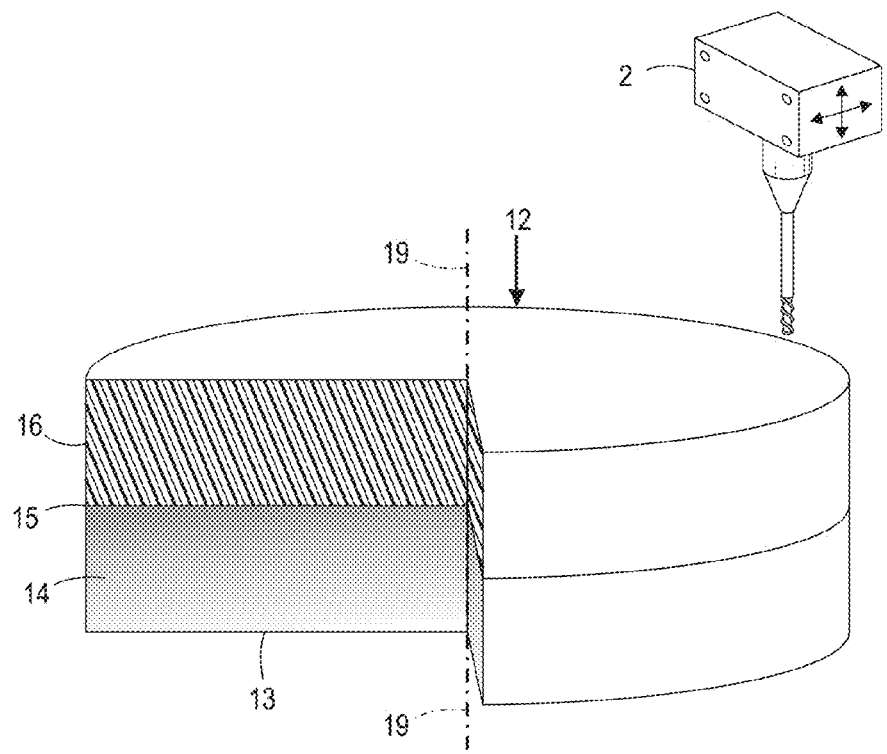
FIG. 2A is a cutaway illustration of a block of denture material comprising a layer of denture base material contiguous at an interface with a layer of denture tooth material, and a schematic illustration of a milling machine for forming a preliminary try-in denture from the block.

FIG. 2A is a cutaway illustration of a block 12 of denture material, and a schematic illustration of a milling machine for forming a preliminary try-in denture from the block 12. The block 12 is comprised of a layer 16 of denture base material contiguous at an interface 15 with a layer 14 of denture tooth material. The denture base material 16 and denture tooth material 14 are suitably biocompatible and structurally strong materials, and may be polymer materials, such as polymethylmethacrylate (PMMA). The denture base material 16 preferably includes a pigment or dye that results in pink coloration that matches the pink color of gum tissue.

Figure 2B:
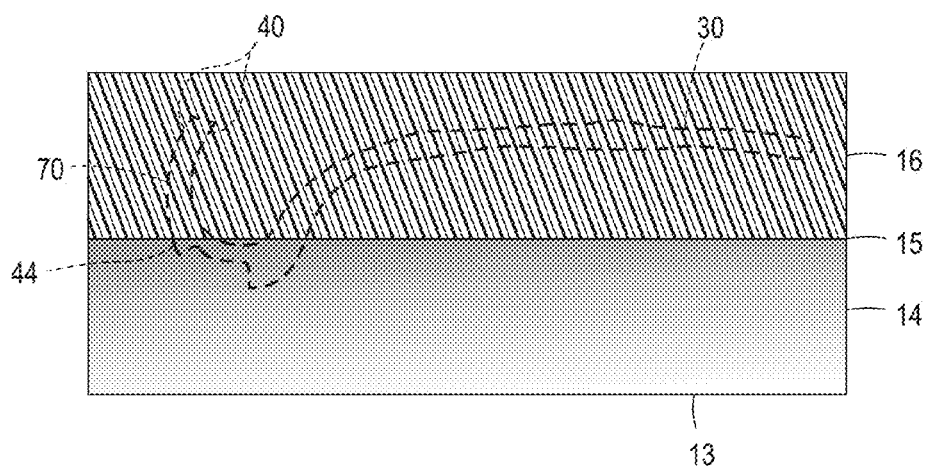
FIG. 2B is a schematic cross-sectional illustration of the block of denture material of FIG. 2A, further illustrating the portions of a denture that are made from the denture base material and the portions that are made from denture tooth material.

In certain embodiments, the layer 14 of denture tooth material may be non-homogeneous, having a gradient of translucency from lowest translucency to highest translucency along a first axis 19. Referring again to FIGS. 2A and 2B, the gradient of lower translucency near interface 15 to higher translucency near the bottom 13 of the layer 14 is indicated by variable shading from darker to lighter along axis 19. In such embodiments, the block 12 is oriented as shown during forming the posterior denture teeth 53, the denture base palatal region 30 and the flange region 40.

Additionally, the anterior denture teeth 51 that are to be included in the final completed denture 10 may also be formed from the denture tooth layer 14 of the block 12, or a separate block (not shown) of denture tooth material having the translucency gradient. Referring also to FIG. 14B, it can be seen that as a result of the orientation of the block 12 (and optional other block of denture tooth material) with translucency gradient along axis 19, the anterior denture teeth 51 are formed with lower translucency at bases 52 of the teeth 51 and higher translucency at outer extremities 54 of the teeth 51. In that manner, the anterior teeth 51, as well as the posterior teeth 53 that also have the translucency gradient effect, have a more natural appearance.

In one exemplary embodiment, the synthetic teeth 50 with translucency gradient may be made from a solid block of polymethylmethacrylate (PMMA) which is formulated as a complex material with a varying amount of white pigment particles that results in a translucency gradient in the layer 14 of the block 12 from which the teeth 50 are formed. Other suitable materials are dental composite and translucent zirconia. In one exemplary embodiment, a multi-layer PMMA material manufactured by Huge Dental has been used. The material has a flexural strength greater than 50 MPa, a water solubility less than 7.5 µg/mm$^3$ and a water absorption less than 40 µg/mm$^3$.

The first-milled denture used in the present method is made by suitable processes, such as vacuum molding, additive manufacturing, laser ablation, or milling. In the embodiments depicted in FIGS. 2A-5, the first-milled denture is made by milling a block (or separate blocks) of denture material. The first-milled denture may be defined using a computer and CAD software as three-dimensional digital models.

Figure 3A:
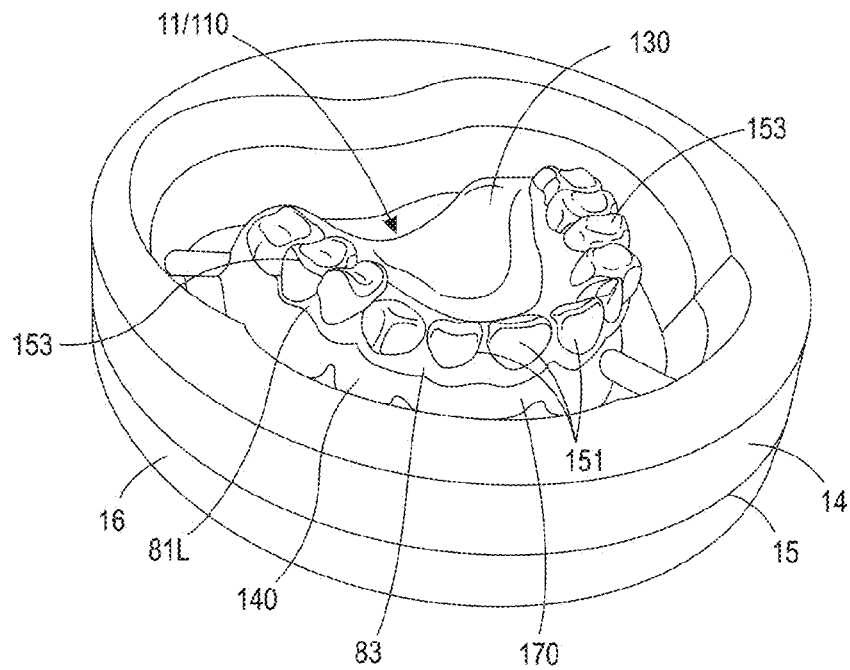
FIGS. 3A and 3B are perspective and bottom views of a first-milled denture formed from the block of denture material.
Figure 3B:
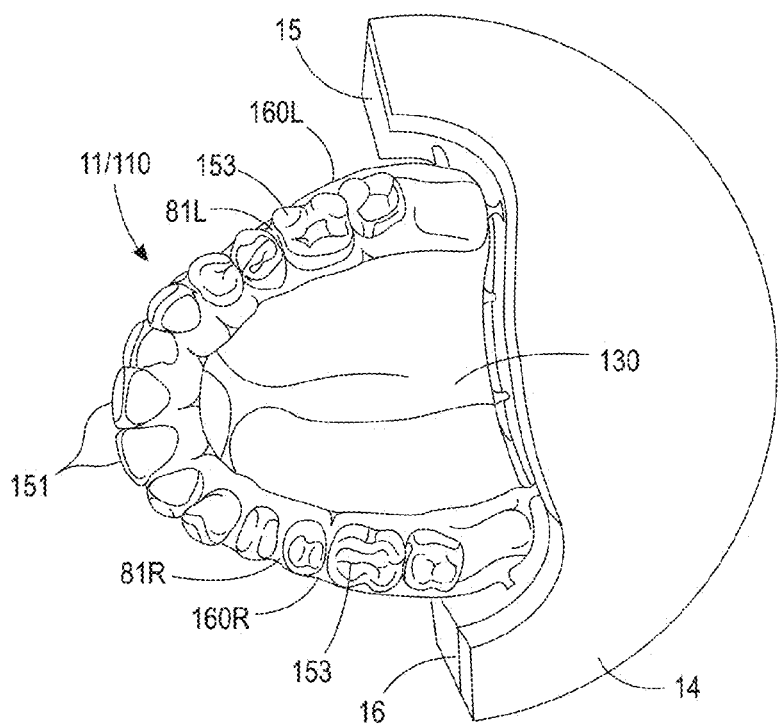

The three dimensional model of the denture may be uploaded to a suitable computer numerically controlled (CNC) fabrication machine, such as milling machine 2. The milling machine 2 is operable to selectively remove denture base material and denture tooth material from the block 12 in a manner similar to that described in commonly owned U.S. Pat. No. 8,641,938, the disclosure of which is incorporated herein by reference. Referring to FIGS. 2A, 3A, and 3B, the milling machine removes denture base material from layer 16 and denture tooth material from layer 14 to form the first-milled denture 110 including a first-milled denture base comprising palatal region 130, first-milled flange region 140, first-milled buccal regions 160L and 160R, first milled labial region 170, and first-milled posterior denture teeth 153 and first-milled anterior denture teeth 151. (Although the first-milled denture 110 is depicted in FIGS. 3A and 3B as having been made from a two-layer block of material, it is not required that the first-milled denture 110 be made with two layers. However, in embodiments in which the first-milled denture 110 is made from two-layer material, after it is used to form the preliminary mold 90 of FIG. 4B, it can be "converted" to the preliminary try-in denture by further milling to remove the anterior teeth and form gingival recesses, as described below.) The first-milled denture 110 may be used as a preliminary denture, and subsequently further processed by replacing tooth colored gingival material with natural-looking denture material to produce a completed denture in a minimum of steps, as will be described subsequently herein. The completed denture, being mad with minimal processing steps, is useful as a low-cost "economy" denture.

Figure 5:
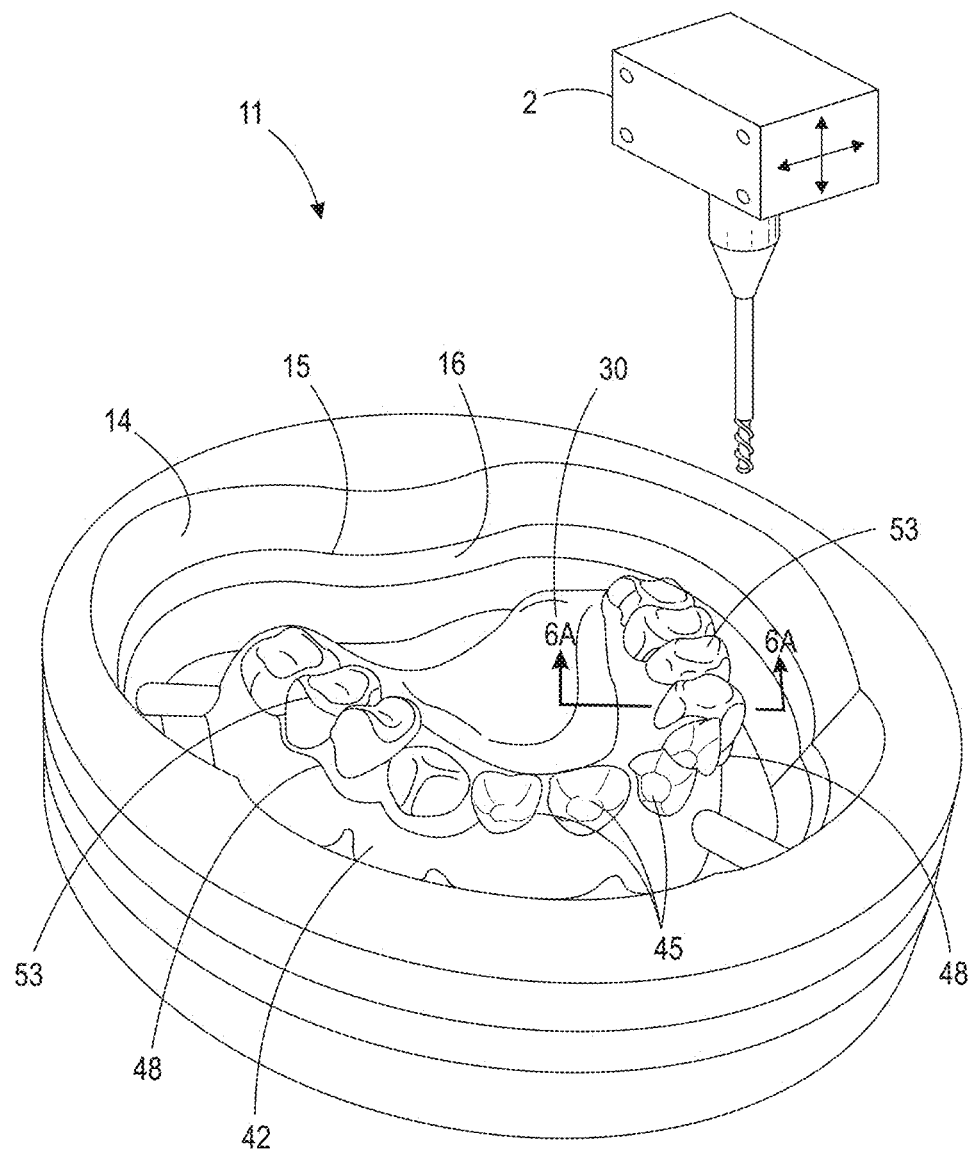
FIG. 5 is a perspective view of a second-milled denture with anterior teeth removed and having anterior tooth recesses.

The preliminary try-in denture may also be made using the milling machine 2. Referring to FIG. 5 and to FIG. 3A, the milling machine 2 forms the preliminary try-in denture 11 by milling a block 12 of denture material including a layer 16 of denture base material and a layer 14 of denture tooth material. The mill 2 removes denture base material from layer 16 to form the palatal region 30 of the denture base, as well as denture base material 16 to form the flange region 40 of the denture base. The mill 2 also removes denture tooth material from layer 14 to form the gingival portions of the denture base, i.e., buccal gingival regions 81L and 81R, and labial gingival region 83.

As noted above, in one embodiment, the first-milled denture 110 may be fabricated as depicted in FIGS. 3A and 3B, and used for making a preliminary mold 90 as will be described subsequently herein with reference to FIGS. 4A and 4B. Then, the first-milled denture 110 may further milled to form the preliminary try-in denture 11. Referring to FIGS. 3A and 3B, it can be seen that the mill 2 is operated so as to form the palatal region 30 and a first (upper) portion 42 of the gingival regions from the layer 16 of denture base material. Additionally, the entire set of posterior teeth 153 and anterior teeth 151 are milled from the layer 14 of denture tooth material. Referring again to FIG. 5, in an additional step in making the preliminary try-in denture 11 from the first-milled denture 110, the mill 2 removes denture tooth material from layer 14, removing the anterior teeth 151 and forming anterior tooth sockets 45.

It is noted that at this point, the buccal gingival regions 81L and 81R, and labial gingival region 83 of the denture base of the first milled denture 110 are made from the denture tooth material. This occurs because the location of the gingival regions 81L, 81R, and 83 varies in vertical position from tooth-to-tooth. Thus there is no single plane in the denture 110 above which is denture base material, and below which is denture tooth material. This results in a problem, in that the gingival regions proximate to the teeth, being of white denture tooth material, do not look natural, and any denture made in this manner would have an unsatisfactory aesthetic appearance.

To solve this problem, in the buccal gingival regions 81L and 81R, and the labial gingival region 83, additional denture tooth material may be cut away, i.e., milled out, forming exterior gingival recesses and interior gingival recesses. Subsequently, these exterior gingival recesses and interior gingival recesses may be filled with pink denture base material, since they are visible to the wearer of the denture and others, in order to provide the finished denture with a pleasing aesthetic appearance.

Figure 6A:
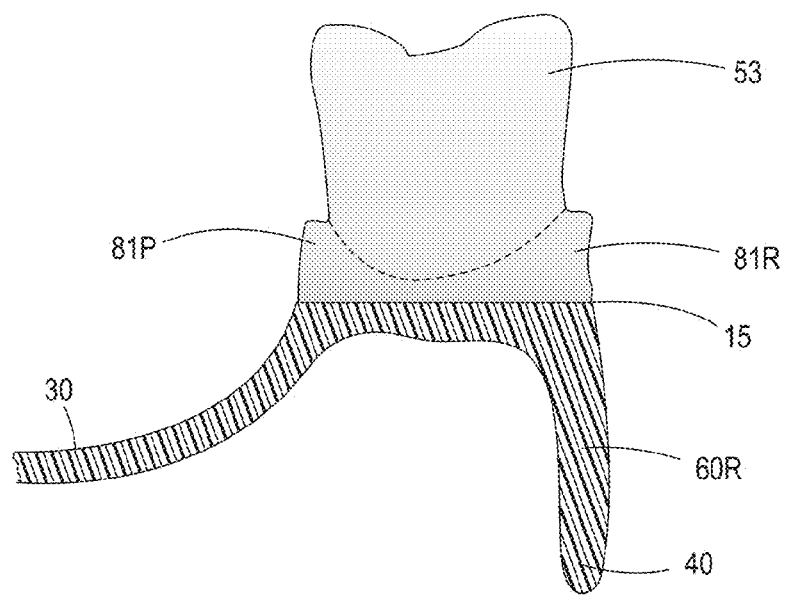
FIG. 6A is a cross-sectional view of a right molar region of the partially fabricated first-milled denture, taken along line 6A-6A of FIG. 5.

These steps will now be described in detail with reference to FIGS. 6A-6G. FIG. 6A is a cross-sectional view of a right molar region of the partially fabricated first-milled denture 11, taken along line 6A-6A of FIG. 5. The milling steps up to this point have formed the posterior tooth 53 from the denture tooth material 14 and the flange 40, buccal region 60R, and palatal region 30 of the denture base from denture base material 16. Additionally, the buccal gingival region 81R and the corresponding interior palatal gingival region 81P have been made from denture tooth material, which is contiguous at the interface 15 with the denture base material. In the milling to form these regions, the location of the interface 15 between the denture tooth material 14 and denture base material 16 is chosen so that all of the denture teeth are made from denture tooth material. This results in "high points" in the gingival regions along the centerlines of the teeth being made of denture tooth material. Thus these gingival regions that are made of denture tooth material, including buccal gingival region 81R and palatal gingival region 81P, must be milled out and replaced with denture base material in order for the denture to have a natural appearance. (In an alternative embodiment, the interface between the denture tooth material and denture base material could be located so that all of the gingival regions are made of denture base material. However, this would result in areas of the teeth near the gingival regions being made of denture base material, which would have to be milled out and replaced with denture tooth material. This is a less desirable alternative.)

Figure 6B:
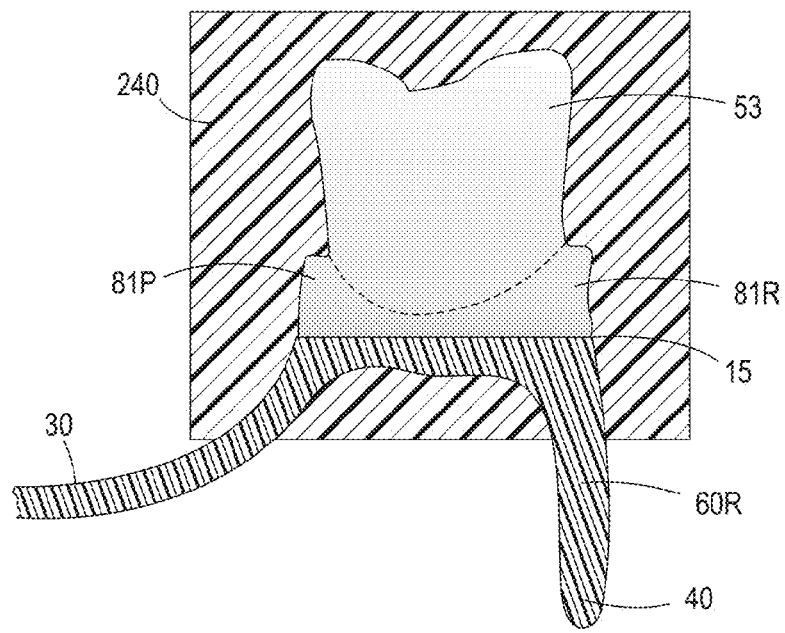
FIGS. 6B-6F are cross sectional views of the right molar region of the partially fabricated first-milled denture that depict a series of steps to provide denture base material in the gingival areas of the first-milled denture.

Referring to FIG. 6B, an index or impression 240 is made of the posterior denture teeth 53, anterior denture teeth denture teeth 51, palatal gingival regions including region 81P, labial gingival regions, buccal gingival regions including region 81R, and nearby portions of the palatal region 30, labial region, and buccal regions including region 60R of the denture base. The index 240 may be made by casing a suitable molding elastomer such as silicone rubber around these regions. By forming the index 240, the desired shapes of the denture teeth and nearby gingival regions of the denture base are replicated by the cavity of the index. After the index material is cured into a solid, the index is removed from the first milled denture 11.

Figure 6C:
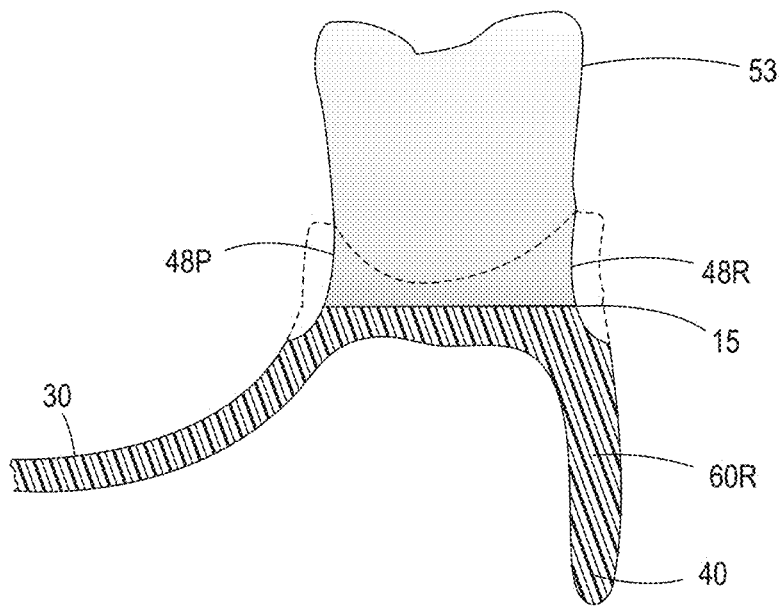

Referring to FIG. 6C, the denture tooth material that forms the gingival regions of the first milled denture, including buccal gingival region 81R and palatal gingival region 81P, are removed by milling. This results in the formation of forming exterior labial and buccal gingival recesses and palatal gingival recesses, including palatal gingival recess 48P and buccal gingival recess 48R. The gingival recesses extend down below the interface 15 into the pink denture base material. In certain embodiments, a depth of about 1.5 to 2 mm of material is milled away to form the gingival recesses.

Figure 6D:
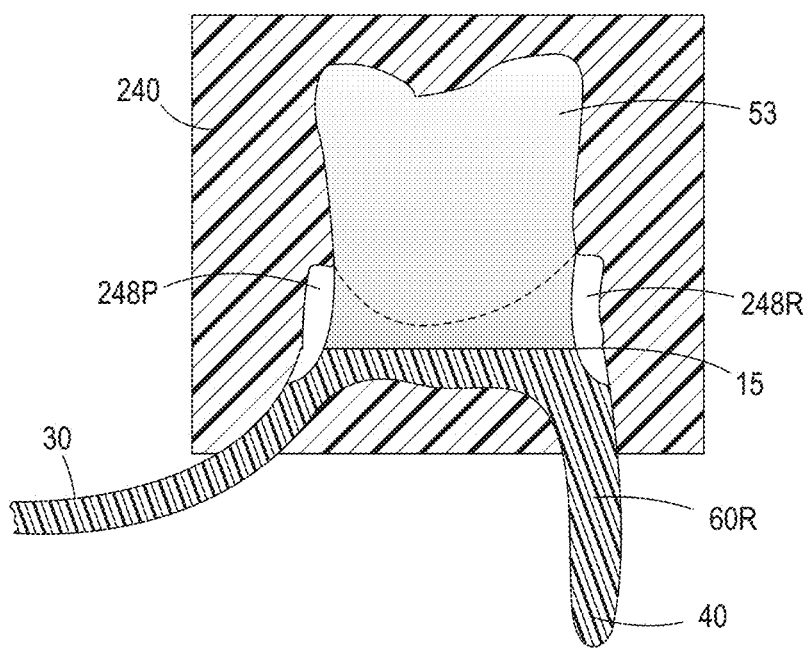

Referring to FIG. 6D, the index 240 is replaced on the first milled denture 11. The gingival portions of the inner cavity of the index, in combination with the gingival recesses, including palatal gingival recess 48P and buccal gingival recess 48R, form gingival mold chambers including chambers 248P and 248R, along the base regions of the denture teeth.

Figure 6E:
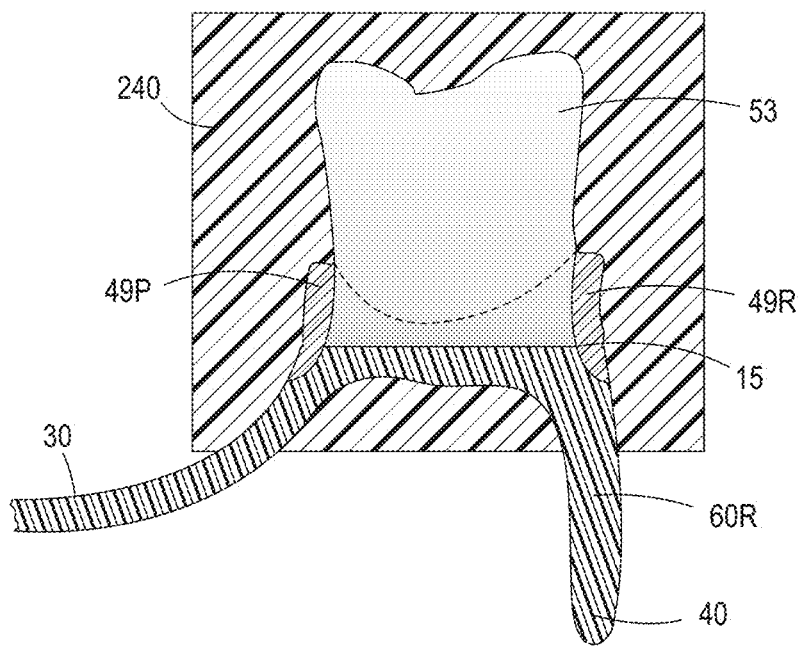
Figure 6F:
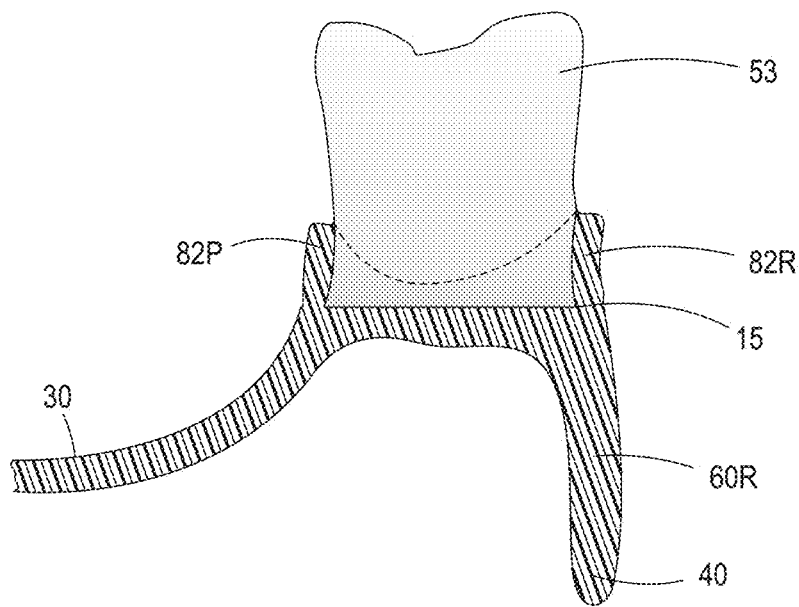

Referring to FIG. 6E, in an embodiment in which the resulting denture is to be used immediately by a patient (i.e., an "economy denture"), instead of as a try-in denture, liquid denture base material is poured or delivered by a suitable fluid delivery system (not shown), filling the gingival mold chambers which are accessed by a sprue hole (not shown) in the index material 240. This liquid denture base material is a "final" denture base material, in that upon curing, it will replace the second portion of the gingival regions of the denture base that were previously formed of denture tooth material with denture base material that "blends in" with the adjacent denture base material of the palatal, labial, buccal, and flange regions of the completed denture. The liquid denture base material in the gingival mold chambers, including material 49R and 49P that fill respective chambers 248P and 248R, is cured into solid color-matched pink denture base material. The index 240 is then removed from the first milled denture 11. Referring to FIG. 6F, the right molar region of the completed first milled denture 11 is shown. It can be seen that the gingival regions 82P and 82R that have been formed blend contiguously into the nearby respective palatal region 30 and buccal region 60R. The entire gingival region of the denture base blends contiguously with nearby regions of the denture base. In that manner, the first milled denture, which is useable as an economy denture, has a natural and aesthetically pleasing appearance.

In an alternative embodiment of making an economy denture, the first-milled denture 11 is formed so as to include the gingival recesses, including gingival recesses 48P and 48R as shown in FIG. 6C. Then, instead of encasing the first-milled denture 11 in an index 240 as shown in FIG. 6D to form gingival mold chambers including chambers 248P and 248R, a dental technician fills the gingival recesses with a suitable denture base material, using a technique similar to that of filling a tooth cavity. The material may be a composite material similar to such materials as are used in tooth fillings, but with a colorant that provides a pink color that matches natural gingival tissue. The material may be a semi-solid paste or putty-like material, which is cured to a solid by ultraviolet light.

Although the preliminary try-in denture 11 comprised of the denture base palatal region and gingival region and the posterior denture teeth is described herein as being made by further milling of the first-milled denture of FIGS. 3A and 3B, it will be apparent that the preliminary try-in denture 11 of FIG. 5 could be made starting "from scratch" with a new block 12 of two-layer denture material.

A preliminary mold is made for use in combination with the preliminary try-in denture 11 to make a complete try-in denture that can be fitted to the patient, for the purpose of making final adjustments so that the final complete denture has an optimal aesthetic appearance and fit to the patient. The preliminary mold may be made using various methods. In certain embodiments, the preliminary mold may be made by digitally scanning the preliminary try-in denture, and using the digital data to operate a CNC milling machine that fabricates the mold. Alternatively, the mold may be made by an additive manufacturing process. The additive manufacturing process may be selected from fused deposition modeling, selective laser melting, selective laser sintering, selective heat sintering, stereolithography, robocasting, electron beam freeform fabrication, direct metal laser sintering, electron bean melting, binder jetting, and digital light processing. In other embodiments, the adjusted temporary denture may be encased in a mold material to form the mold, such as by vacuum molding. The preliminary try-in denture is then removed from the vacuum-formed mold.

Figure 4A:
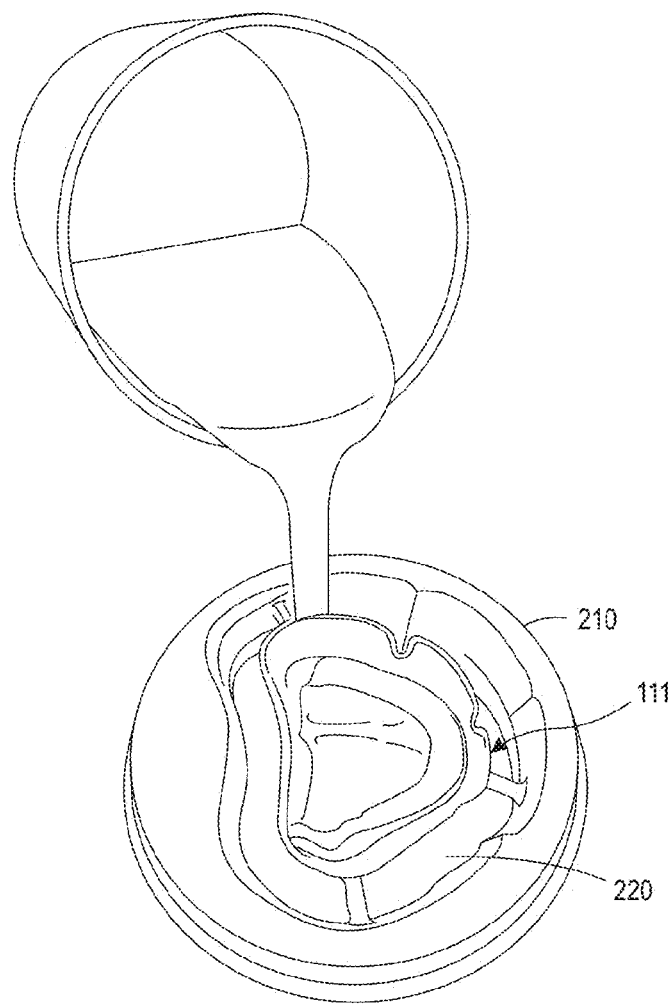
FIG. 4A is a perspective view of a step for forming a preliminary mold of the first-milled denture.
Figure 4B:
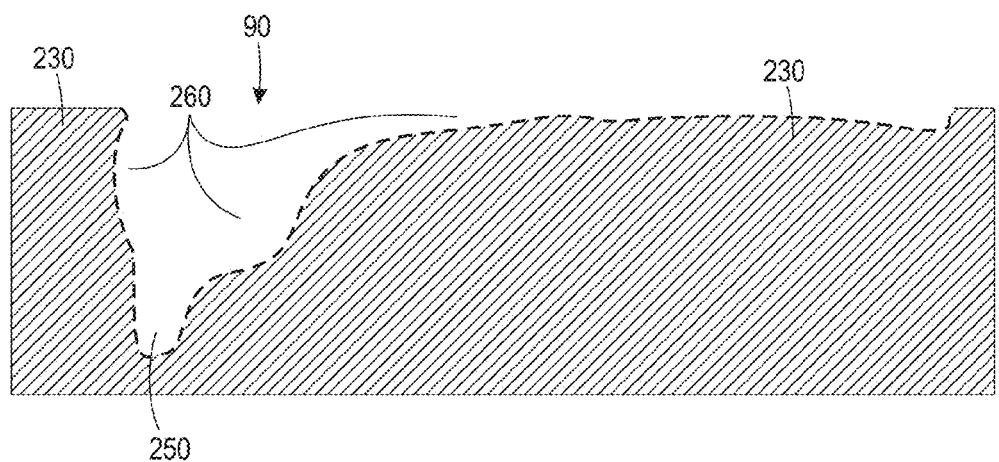
FIG. 4B is a cross-sectional view of the preliminary mold resulting from the mold forming step depicted in FIG. 4A.

Alternatively, in an embodiment depicted in FIG. 4A, a preliminary mold is made by encasing the first-milled denture 110 in a mold casting material such as liquid silicone. The first-milled denture 110 may be placed in a mold vessel 210, and at least partially immersed in a liquid molding material 220. The liquid molding material 220 is cured to a solid or semi-solid material 230. The first-milled denture 110 is then removed, resulting in the preliminary mold 90 of FIG. 4B, having a mold cavity including anterior tooth cavities 250, posterior tooth cavities (not shown), and a denture base cavity 260. Alternatively, a silicone putty (addition-reaction or condensation-type) may be used to form the mold (index).

Figure 7:
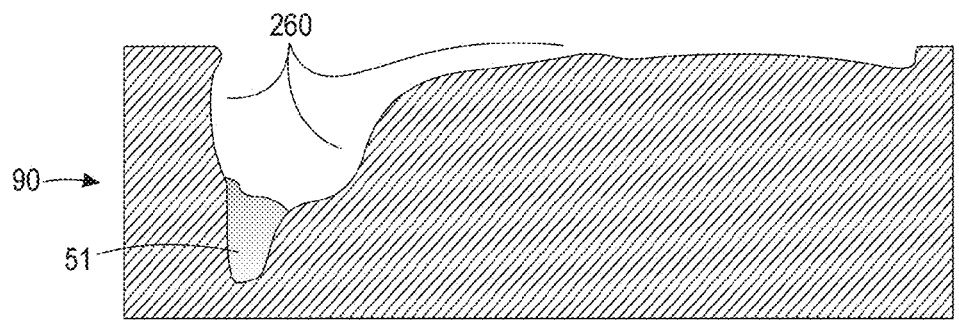
FIG. 7 is a cross-sectional view of the preliminary mold of FIG. 4B, with anterior teeth disposed in anterior tooth recesses of the preliminary mold.
Figure 8:
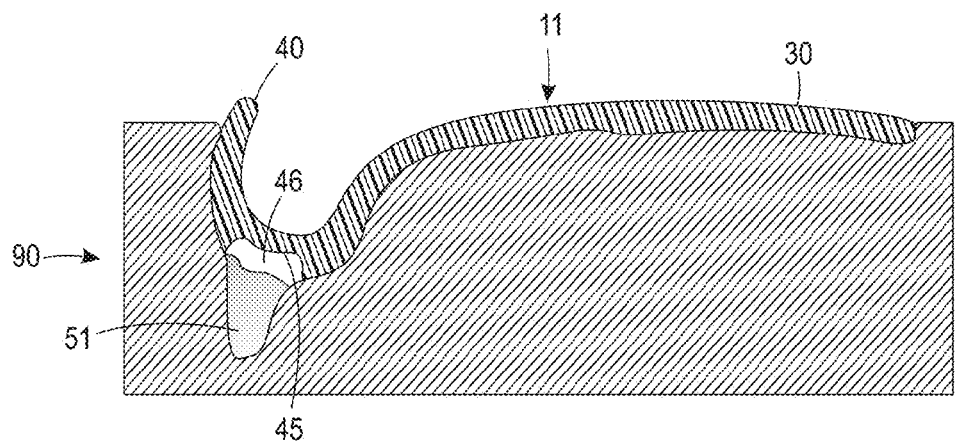
FIG. 8 is a cross-sectional view of the preliminary mold and anterior teeth of FIG. 5, additionally with the second-milled denture disposed in the preliminary mold, and the anterior tooth recesses thereof proximate to the anterior teeth that are disposed in anterior tooth cavities of the preliminary mold.
Figure 9:
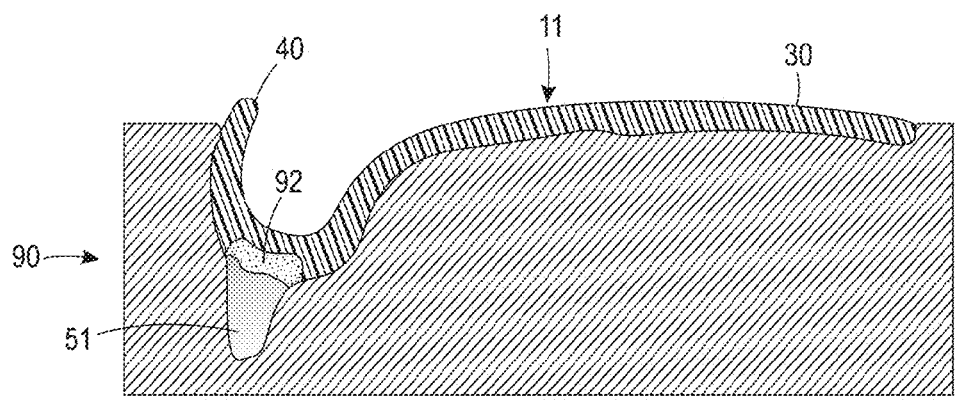
FIG. 9 is a cross-sectional view of the preliminary mold, anterior teeth, preliminary try-in denture of FIG. 8, and a deformable solid wax disposed in anterior tooth chambers in the preliminary mold, forming a complete try-in denture.

Referring to FIG. 7, a plurality of anterior denture teeth 51 are then disposed in the anterior tooth cavities 250 of the preliminary mold 90. The anterior denture teeth 51 have the same respective dimensions as the first-milled anterior denture teeth 151. The anterior denture teeth 51 may be made from a denture tooth material having a translucency gradient as described previously. Each anterior denture tooth 51 is disposed in a correspondingly dimensioned anterior tooth cavity 250 of the preliminary mold 90. Referring to FIG. 8, the second-milled denture 11, which does not include anterior teeth, is then disposed in the mold cavity of the preliminary mold 90 with the posterior teeth 53 disposed in the posterior tooth cavities and the denture base including flange region 40 and palatal region 30 disposed in the denture base cavity 260. Referring to FIG. 9, a deformable solid wax 92 is then disposed in the tooth chambers 46 bounded by the bases of the anterior denture teeth 51 and the anterior tooth sockets 45. In certain embodiments, the tooth sockets that form the chambers 46 may have a depth of between 1 and 3 mm. The deformable solid wax 92 may be first provided in liquid form, and delivered through one or more sprues (not shown) that are formed in the mold 90. The delivery of the liquid phase wax may be performed manually using a suitable device such as a syringe, or by a suitable fluid delivery system such as a metering pump or a syringe pump. The wax 92 solidifies and temporarily joins the individual anterior teeth 51 to the second-milled denture 11, to form the complete try-in denture 18 (FIG. 10), while rendering the individual anterior teeth 51 adjustable during a try-in on the patient to whom the complete try-in denture 18 is being fitted. Additionally, if gingival recesses have been formed as previously described and shown in FIG. 6C, the liquid wax may be delivered and solidified in any such exterior and/or interior gingival recesses 48 (FIG. 5) that are provided in the second-milled denture 11.

Figure 10:
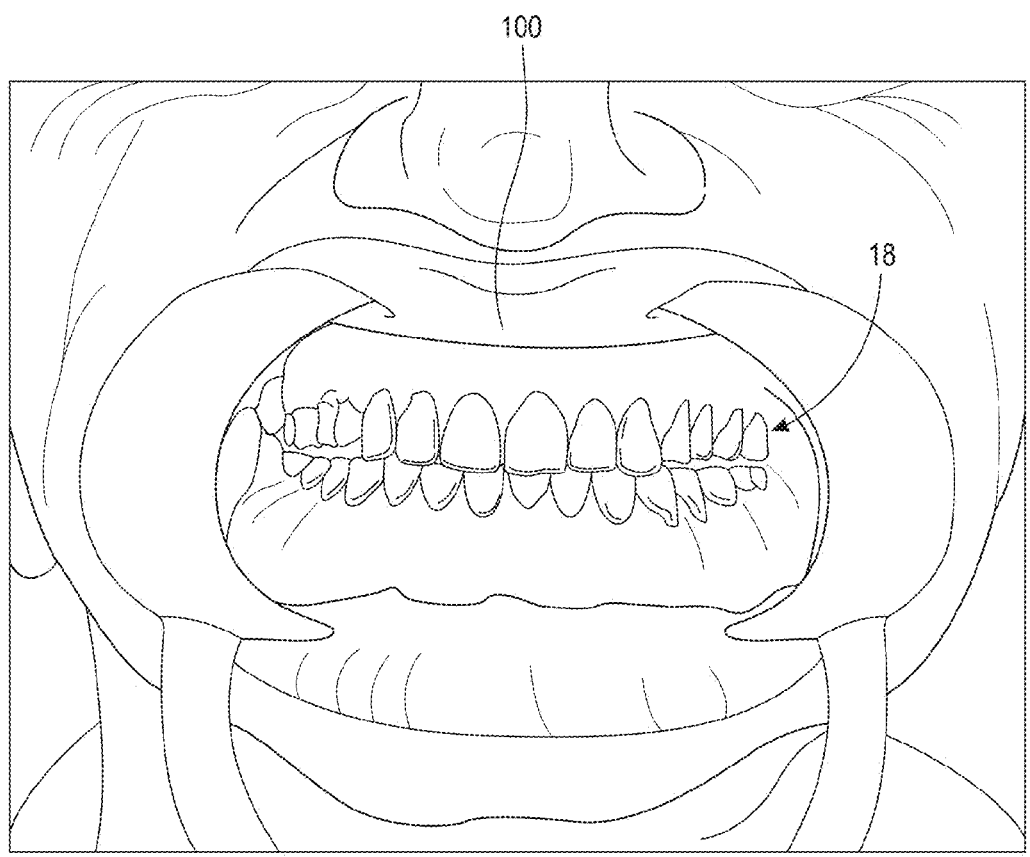
FIG. 10 is a perspective view of the complete try-in denture of FIG. 9, removed from the preliminary mold and fitted to a patient for optimization of fit to the patient, producing an adjusted try-in denture.

Referring to FIG. 10, the complete try-in denture 18 is then removed from the preliminary mold 90 and fitted to the mouth 100 of the patient/wearer of the denture 18, and modified to adjust the fit thereof to the mouth 100 of the patient. The dental practitioner (not shown) checks the temporary denture 18 for proper occlusion, speech, lip support, smile line, tooth position and general aesthetics. The wax 92 that is disposed between the denture base material and the anterior teeth 51, and also in optional exterior and interior gingival recesses 48 is a solid material that has a low yield point and is subject to deformation when a threshold stress is applied. In that manner, the positions of the anterior teeth (and/or posterior teeth, if milled away in the second-milled denture) can be adjusted by the dental practitioner during a try-in of the complete try-in denture 18 on the patient 100. The dental practitioner may make adjustments to the position of the anterior teeth 51 by gently forcing the teeth 51 upward or downward or anteriorly or posteriorly, deforming the wax 92 as needed to make the adjustments. (In some cases, the wax may be softened prior to movement by the application of heat). The dental practitioner may also reform the wax 92 in the exterior and interior gingival recesses 48 to result in a natural appearance of the outer gingival region of the denture and proximate denture teeth, and as needed for as needed for optimal fit and maximum comfort of the patient. As used herein, the term "wax" is not limited to simple low molecular weight hydrocarbon waxes such as "candle wax," but encompasses any suitable biocompatible non-toxic water insoluble material that has a sufficiently low yield point to deform when stress is applied by the dental practitioner to adjust the position of the teeth, and to cease deforming when the dental practitioner stops adjusting position, so that the teeth maintain their adjusted position. Suitable wax materials include, but are not limited to dental compound, clay and clay-like materials, polymer compounds that are not fully polymerized such as PMMA, urethane, composites, polyvinyl siloxanes, rubber based materials and silicones.

Additionally, the posterior teeth 53 of the complete try-in denture 18 may be adjusted for optimal occlusion by using articulating paper and a bur to locate "high spots" and then grinding each "high-spot" down in progressive steps. A jaw recording device (not shown), such as a Gothic Arch tracing system (e.g., a Massad Jaw Recorder) may be used to make this process efficient and accurate. The borders of the complete try-in denture 18 may be evaluated for fit and further adjusted as required. The patient 100 may also comment on areas that feel tight or cause pressure on their dental ridge, and those areas can be adjusted, such as by grinding with a bur. In some cases, a pressure indicating paste may be used to determine where interferences are present, and then those interferences are adjusted.

Once the adjustments are completed, the resulting adjusted try-in denture 19 is removed from the mouth 100 of the patient. A mold of the adjusted try-in denture 19 is then formed. This mold is a "final" mold because its denture base and denture teeth dimensions correspond to the shapes of the adjusted temporary denture 19, which has been adjusted for optimal fit to the patient, and therefore define the desired shape of the final completed denture 10 (FIG. 14A).

Figure 11A:
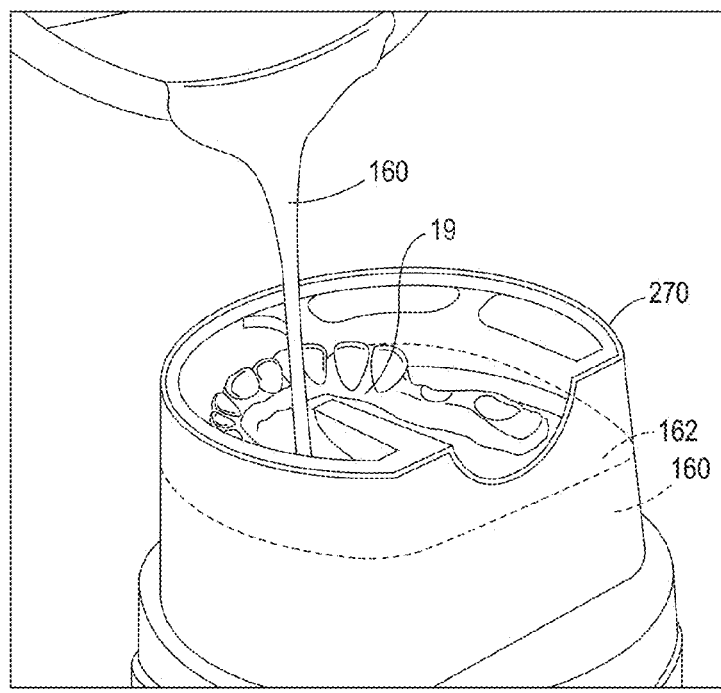
FIGS. 11A and 11B are schematic illustrations of steps of making a final mold of the adjusted try-in denture.
Figure 11B:
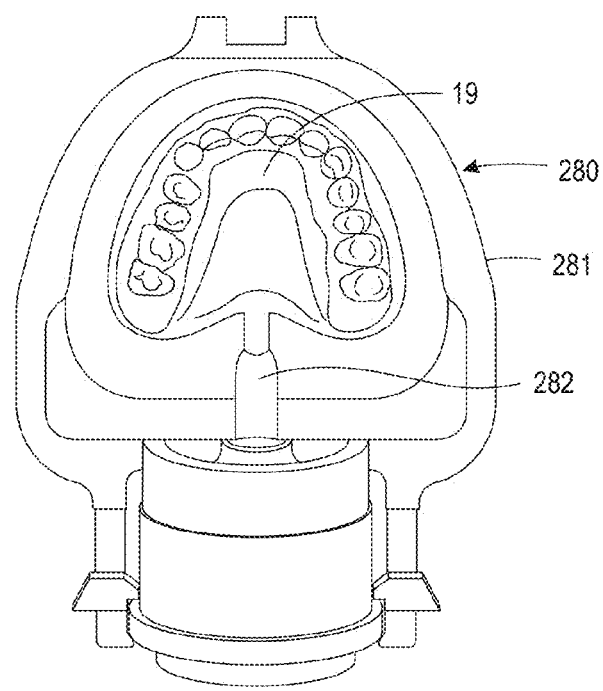

The final mold may be made by vacuum molding or other suitable molding processes, as described previously herein. Alternatively, the final mold may be made by methods as shown in FIGS. 11A and 11B. In the embodiment depicted in FIG. 11A, the adjusted temporary denture 19 is placed in a mold flask 270. In one embodiment of FIG. 11A, the adjusted temporary denture 19 may be encased in agar. The agar solidifies, and can be removed as a single piece from the mold flask 170, with the adjusted temporary denture 19 contained therein. The solid agar can then be cut into two portions and separated. The adjusted temporary denture 19 is removed from one of the portions, leaving the two agar pieces forming the final denture mold.

In another embodiment of FIG. 11A, the adjusted temporary denture 19 may be partially encased in liquid silicone 160 or silicone putty (not shown). The liquid silicone 160 is then cured to form a solid silicone rubber half with a planar interface corresponding to the upper surface 162 of the liquid silicone 160 and surrounding a portion of the adjusted temporary denture 19. A thin film of release agent, such as Vaseline® petroleum jelly, may be applied to the interface. The remaining exposed portion of the adjusted temporary denture 19 is then encased in liquid silicone 160, which is then cured into solid silicone rubber. The entire silicone rubber and adjusted temporary denture 19 are removed from the mold flask 270. Due to the use of the release agent, the silicone rubber lower and upper portions are easily separated. The adjusted temporary denture 19 is removed from one of the portions, leaving the two silicone rubber pieces forming the final denture mold.

In the embodiment depicted in FIG. 11B, the final mold is formed by placing the adjusted temporary denture 19 into a flask 280 including a first half 281, and a second half (not shown). The two halves of the flask 280 are joined together, and a slurry of liquid dental stone material may be delivered into one half of the flask 280, then a separating medium (e.g., Vaseline®) is applied to the hardened surface. A second pouring of dental stone on top of the first half then solidifies into a solid, this forming a mold that encases the adjusted temporary denture 19. The dental flask halves are separated and the dental stone mold and adjusted temporary denture 19 are removed from one of the flask halves. The stone mold may then be split into two pieces, and the adjusted temporary denture 19 removed from the piece that contains it. In certain embodiments, the dental flask 280 may be provided with a sprue 282, which forms a channel in which liquid denture base material will be poured, injected, or press-packed into in a subsequent step of denture fabrication.

The final mold of the denture includes final anterior tooth cavities, final posterior tooth cavities, a final palatal cavity, final labial, buccal, gingival, and flange cavities; and (optionally) final gingival cavities, the dimensions of which result from the adjustments made by the dental practitioner to optimize the fit and appearance of the try-in denture in the patient. The anterior denture teeth 51 are removed from the adjusted try-in denture 19, and the deformable solid wax material 92 contained in the gingival recesses and anterior tooth sockets is removed from the adjusted try-in denture 19 using steam to melt the wax, or hot water or other suitable wax removal media including a solvent that dissolves the wax. With the anterior denture teeth 51 and solid wax 92 removed from the adjusted try-in denture 19, a semi-complete denture is formed.

The anterior denture teeth 51 are placed in corresponding final anterior tooth recesses in the final mold of the denture. The semi-complete denture is then placed in the final mold of the denture with the posterior denture teeth 53 disposed in corresponding final posterior tooth recesses, the palatal region 30 disposed in the final palatal cavity, and the and the labial, buccal, gingival, and flange regions disposed in the respective final labial, buccal, gingival, and flange cavities.

Figure 12:
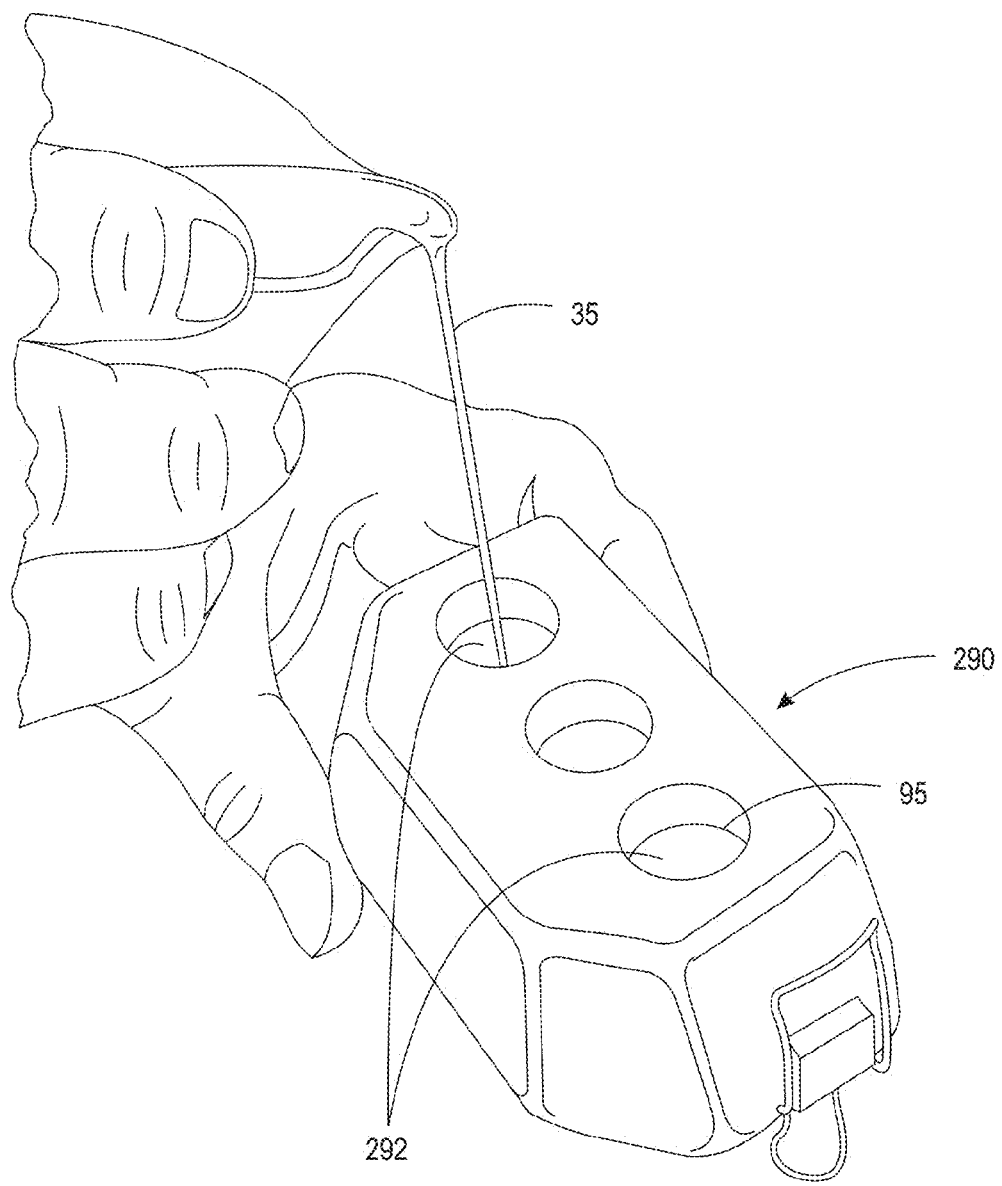
FIG. 12 is a perspective view of a step for filling gingival chambers in the final mold to form a completed denture.

Referring to FIG. 12, the final mold 95 of the denture is placed in a flask 290. Liquid or dough-like final denture base material 35 is then delivered into the final mold. The liquid or dough-like final denture base material 35 may be delivered using sprues 292, thereby filling the anterior tooth chambers bounded by the bases of the anterior teeth 51 and the anterior tooth sockets 45 formed in the denture base, and the gingival chambers bounded by the gingival recesses and final gingival cavities of the final mold 95. In certain embodiments, the liquid final denture base material may be liquid or dough-like polymethylmethacrylate (PMMA), which upon curing, chemically bonds to the PMMA denture tooth material of the rest of the denture structure. The PMMA preferably includes a pigment or dye that results in pink coloration that matches the pink color of natural gum tissue.

In other embodiments, other denture base materials may be substituted for the pourable PMMA material. Such other materials may be light cured materials (urethane based and other types). Alternative other materials may be self-polymerizing resins such as silicones which may be poured or injected into the sprues. Other materials that may be injected include polyamides and other thermoplastics. Materials that are not "pourable" may be hand-applied to the areas milled with voids to make space for the pink-toned materials. These hand-applied materials may include silicones, composite or materials made from additive manufacturing methods such as 3D printing. In another embodiment, the void areas may be filled with wax, and then the wax may be removed and thoroughly cleaned from the surface of the void areas; then the void areas may be filled with tissue-toned denture base material as described above or using conventional lost-wax techniques for denture processing such as packing and injecting denture base resins.

Figure 13A:
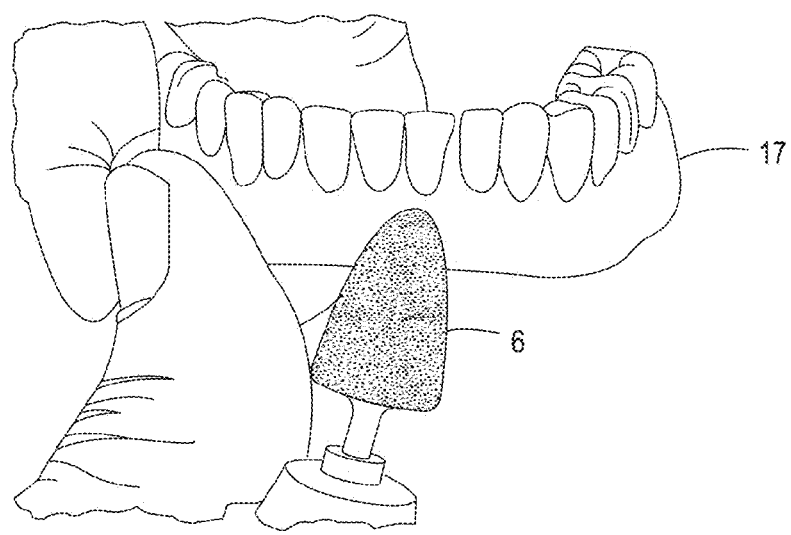
FIG. 13A is a perspective view of a first step for finishing a completed denture removed from the mold of FIG. 12 to a finished denture.
Figure 13B:
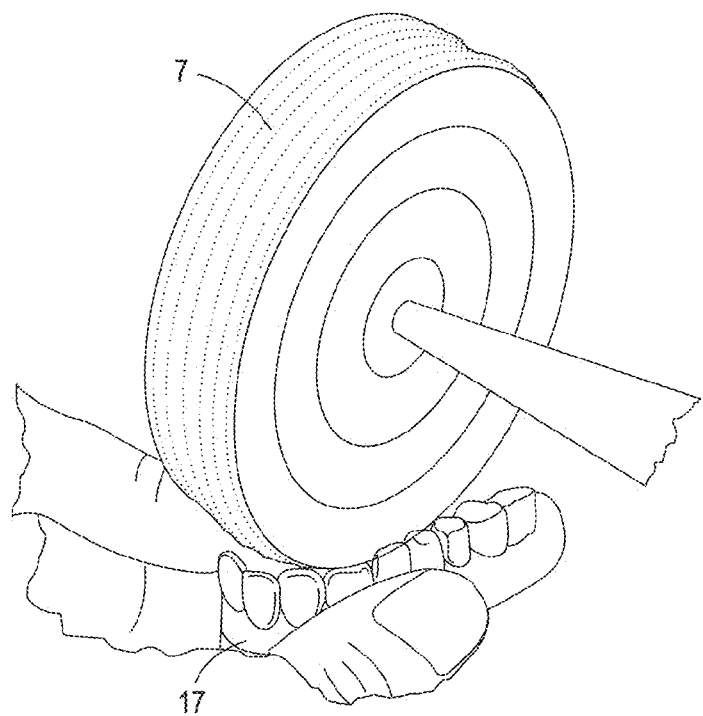
FIG. 13B is a perspective view of a second step for finishing the completed denture to produce the finished denture.

The final denture base material is cured to form a completed denture, which is removed from the final mold 95. Referring to FIGS. 13A and 13B, the completed denture 17 may then be polished or otherwise finished as needed using grinding tool 6 and polishing wheel 7 to remove the sprues and any imperfections, and produce the final denture 10 of FIGS. 14A and 14B ready for fitting to and use by the patient.

The Applicant's denture fabrication method is advantageous over conventional denture fabrications methods for a number of reasons:

1) The method results in a denture that has a better fit with the patient. In conventional practice, in a "try-in" appointment, the "try-in" denture is normally made on a rigid baseplate that does not accurately reflect the final denture. The baseplate is typically made short of the border of the denture because the purpose is not to gauge fit of the denture, because the main purpose of the baseplate is to serve as a platform for the trial denture that is made of pink wax and artificial denture teeth. The main purpose of the "try-in" visit is for the dentist to determine if the occlusion (fitting of the upper and lower arches) is correct, and if speech is acceptable, and vertical dimension of occlusion is proper, etc. In contrast, in the present method, the "try-in" denture base is part of the final denture. This enables the clinician to also evaluate fit of the denture, such as the peripheral borders. (This is one of the most important aspects of a denture—it keeps the denture on the patient's ridge and prevents food from getting under the denture and irritating the patient). If the fit is not ideal, then the dentist can perform a "wash impression" technique (using low viscosity polyvinyl siloxane impression material) to capture a better impression of the dental arches. The impression material is placed into the "try-in" denture in the areas that will touch the patient's tissue. When the impression material cures, the "try-in" denture is removed from the mouth and any excess areas are trimmed away with a sharp scalpel.

2) The denture can be finalized in the dentists' office, reducing turn-around time. In conventional practice, a "try-in" denture typically must be returned to the dental lab that fabricated it because the process is laborious and messy, and not well-suited for a dental office. With the present method, the final denture can be easily fabricated in a dental office with some very simple and low-cost equipment and materials. This unique aspect of the method will reduce turn-around time for the denture. It some circumstances, is anticipated that the denture could be made into a "final delivery denture" within 30 minutes, as compared to days or weeks for conventional denture fabrication.

3) Expertise required for tooth set-up is reduced as a consequence of using CADCAM software and fabrication tools.

4) The need for a dental lab to maintain a large stock of denture teeth is eliminated. (Some dental labs carry over $100,000 worth of teeth in their inventories) In addition, the shades, "natural-looking" imperfections, translucency, etc. of the teeth can be custom-made for each denture.

5) An "economy" denture can be made for the patient by skipping the $2^{nd}$ milling step. This procedure enables skipping the try-in appointment, thus saving the patient and the doctor valuable time.

6) In the present method, the final denture delivery appointment is more predictable because the teeth and denture base are the final shapes and positions as determined at the "try-in" appointment. More time can be spent on fit and occlusion at the "try-in" appointment, which significantly reduces time spent at the delivery appointment. In the conventional process of denture fabrication, the "try-in" denture is made from a wax base and artificial teeth. Then this "try-in" denture is processed by a dental lab using a "lost-wax" technique. There can be changes in the shape of the denture base and thus position of the denture teeth from the wax "try-in" denture as compared to the finished denture due to processing errors, which is very common. These potential changes make the final fitting appointment of a denture made with conventional techniques less predictable. Typically, a dentist will spend considerable time making adjustments (grinding teeth to improve occlusion, and trimming borders and areas of impingements that may cause sore spots) at the delivery appointment. This is stressful for the dentist and the patient because both feel that the final denture should simply slide into place at the final appointment. When significant adjustments are made at this appointment, the patient may feel that the denture was not made properly, thus the dentist is "fixing" it.

It is therefore apparent that there has been provided, in accordance with the present disclosure, methods of making dental prostheses. The foregoing description of technology and the invention is merely exemplary in nature of the subject matter, manufacture, and use of the invention and is not intended to limit the scope, application, or uses of any specific invention claimed in this application or in such other applications as may be filed claiming priority to this application, or patents issuing therefrom. The following definitions and non-limiting guidelines must be considered in reviewing the description.

The headings in this disclosure (such as "Background" and "Summary") and sub-headings used herein are intended only for general organization of topics within the present technology, and are not intended to limit the disclosure of the present technology or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

To the extent that other references may contain similar information in the Background herein, said statements do not constitute an admission that those references are prior art or have any relevance to the patentability of the technology disclosed herein. Any discussion in the Background is intended merely to provide a general summary of assertions.

The description and specific examples, while indicating embodiments of the technology disclosed herein, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

To the extent employed herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the words "comprise," "include," "contain," and variants thereof are intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting ingredients, components or process steps, the Applicants specifically envision embodiments consisting of, or consisting essentially of, such ingredients, components or processes excluding additional ingredients, components or processes (for consisting of) and excluding additional ingredients, components or processes affecting the novel properties of the embodiment (for consisting essentially of), even though such additional ingredients, components or processes are not explicitly recited in this application. For example, recitation of a composition or process reciting elements A, B, and C specifically envisions embodiments consisting of, and consisting essentially of, A, B, and C, excluding an element D that may be recited in the art, even though element D is not explicitly described as being excluded herein.

Having thus described the basic concept of the invention, it will be apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be expressly stated in the claims.

I claim:

1. A method of making a denture comprised of a denture base comprising a labial region, buccal regions, gingival regions, and a flange region, and anterior denture teeth and posterior denture teeth joined to the base, the method comprising:
   a) from a block of denture material comprising a layer of denture base material contiguous at an interface with a layer of denture tooth material:
      removing denture base material from the block to form the buccal, labial, and flange regions of the denture base;
      removing denture base material from the block to form a first portion of the gingival regions of the denture base that are contiguous with the interface with the layer of denture tooth material;
      removing denture tooth material to form a second portion of the gingival regions of the denture base that were contiguous with the interface with the layer of denture base material prior to the removing denture base material to form the first portion of the gingival regions; and
      removing denture tooth material to form the posterior denture teeth and anterior denture teeth, thereby forming a preliminary try-in denture including the posterior denture teeth, anterior denture teeth, and the denture base;
   b) encasing the preliminary try-in denture in a mold forming material to form a preliminary mold of a complete try-in denture;
   c) removing the preliminary try-in denture from the preliminary mold, the preliminary mold having a mold cavity including anterior tooth cavities, posterior tooth cavities, and a denture base cavity;
   d) removing denture tooth material from at least a pair of anterior teeth of the preliminary try-in denture to form at least one pair of anterior tooth sockets;
   e) removing a portion of the denture tooth material from the second portion of the gingival regions of the denture base to form gingival recesses proximate to base portions of the denture teeth;
   f) disposing anterior denture teeth in the at least one pair of anterior tooth cavities of the preliminary mold, the anterior denture teeth having the same respective dimensions as the preliminary try-in denture anterior teeth, each anterior denture tooth disposed in a correspondingly dimensioned anterior tooth cavity of the preliminary mold;
   g) disposing the preliminary try-in denture in the mold cavity of the preliminary mold with the posterior teeth of the preliminary try-in denture disposed in the posterior tooth cavities of the preliminary mold and the denture base of the preliminary try-in denture disposed in the denture base cavity of the preliminary mold;
   h) disposing a deformable solid wax in anterior tooth chambers bounded by the bases of the anterior denture teeth and the anterior tooth sockets, and in gingival chambers bounded by the gingival recesses and a gingival cavity portion of the denture base cavity, to form a complete try-in denture;
   i) fitting the complete try-in denture to the mouth of a patient, and modifying the complete try-in denture to adjust the fit thereof to the mouth of the patient, thereby forming an adjusted try-in denture;
   j) removing the adjusted try-in denture from the mouth of the patient, and applying a mold forming material to the adjusted try-in denture to form a final mold of the denture comprising final anterior tooth cavities, final posterior tooth cavities, final labial, buccal, and flange cavities, and a final gingival cavity;
   k) removing the adjusted try-in denture from the final mold, removing the anterior denture teeth from the adjusted try-in denture, and removing the deformable solid wax material from the adjusted try-in denture to form a semi-complete denture including the gingival recesses and anterior tooth sockets;
   l) placing the anterior denture teeth in corresponding final anterior tooth cavities in the final mold of the denture, and placing the semi-complete denture in the final mold of the denture with the posterior denture teeth disposed in the final posterior tooth cavities, and the labial, buccal, gingival, and flange regions disposed in respective final labial, buccal, gingival, and flange cavities;
   m) filling anterior tooth chambers bounded by the anterior denture teeth and the anterior tooth sockets, and filling gingival chambers bounded by the gingival recesses and final gingival cavities of the final mold with a final denture base material; and
   n) curing the final denture base material to form a completed denture.

2. The method of claim 1, wherein the denture is an upper denture further comprised of a palatal region, and the method further comprises forming the palatal region in the completed denture.

3. The method of claim 1, further comprising removing the completed denture from the mold, and polishing the denture base and the denture teeth of the completed denture to produce a finished denture.

4. The method of claim 1, wherein the forming the labial, buccal, gingival, and flange regions of the denture base, and the posterior denture teeth are performed by milling denture base material and milling denture tooth material from the block.

5. The method of claim 1, wherein the denture tooth material of the block is non-homogeneous, having a gradient of translucency from lowest translucency to highest translucency along a first axis, and wherein the block is oriented during forming the posterior denture teeth such that the posterior denture teeth are formed with lower translucency at bases of the teeth and higher translucency at outer extremities of the teeth.

6. The method of claim 1, wherein the anterior denture teeth are formed from a non-homogeneous denture tooth material having a gradient of translucency from lowest translucency to highest translucency along a first axis, and wherein the denture tooth material is oriented during forming the anterior denture teeth such that the anterior denture teeth are formed with lower translucency at bases of the teeth and higher translucency at outer extremities of the teeth.

7. The method of claim 1, wherein the forming the preliminary mold of the denture and the final mold of the denture are performed by vacuum molding.

8. The method of claim 1, wherein the forming the preliminary mold of the denture and the final mold of the denture are performed by milling.

9. The method of claim 1, wherein the forming the preliminary mold of the denture and the final mold of the denture are performed by an additive manufacturing process.

10. The method of claim 1, wherein the forming the preliminary mold of the denture and the final mold of the denture are performed by molding a liquid or putty silicone elastomer.

11. The method of claim 1, wherein the each of the molds includes at least one sprue in fluid communication with the gingival recesses of the respective mold.

12. The method of claim 1, wherein the preliminary try-in denture is defined by a digital three-dimensional model, and wherein the forming the labial, buccal, gingival, and flange regions of the preliminary try-in denture, and the posterior denture teeth from the block of denture material, and the forming the anterior teeth from denture tooth material are performed based upon data from the three-dimensional model.

13. The method of claim 12, wherein the digital three-dimensional model is based upon three-dimensional data obtained from a digital scan of features of the mouth of a patient to whom the denture is to be fitted.

14. A method of making a denture comprised of a denture base comprising a labial region, buccal regions, gingival regions, and a flange region, and anterior denture teeth and posterior denture teeth joined to the base, the method comprising:
   a) from a block of denture material comprising a layer of denture base material contiguous at an interface with a layer of denture tooth material:
      removing denture base material from the block to form the labial, buccal, and flange regions of the denture base, and a first portion of the gingival regions of the denture base that are contiguous with the interface with the layer of denture tooth material;
      removing denture tooth material to form a second portion of the gingival regions of the denture base that were contiguous with the interface with the layer of denture base material prior to the removing denture base material to form the first portion of the gingival regions; and
      removing denture tooth material to form the anterior and posterior denture teeth, thereby forming a preliminary denture including the posterior denture teeth, anterior denture teeth and the denture base;
   b) removing a portion of the denture tooth material from the second portion of the gingival regions of the denture base to form gingival recesses proximate to base portions of the denture teeth of the preliminary denture to form a semi-complete denture; and
   c) filling the gingival recesses with denture base material, thereby replacing the second portions of the gingival regions previously formed of denture tooth material with second portions of the gingival regions formed of denture base material, to form a completed denture.

15. The method of claim 14, wherein the replacing the second portions of the gingival regions previously formed of denture tooth material with second portions of the gingival regions formed of denture base material further comprises:
   a) filling the gingival recesses with a curable denture base material; and
   b) curing the curable denture base material into a solid state.

16. The method of claim 14, further comprising:
   a) prior to the removing the portion of the denture tooth material from the second portion of the gingival regions of the denture base to form gingival recesses, encasing the preliminary denture in a mold forming material to form a mold of the preliminary denture;
   b) removing the preliminary denture from the mold, the mold having a mold cavity including anterior tooth cavities, posterior tooth cavities, and a denture base cavity including gingival cavity regions;
   c) forming a semi-complete denture by removing the portion of the denture tooth material from the second portion of the gingival regions of the denture base to form the gingival recesses;
   d) disposing the semi-complete denture in the mold cavity of the mold;
   e) filling gingival chambers formed by the gingival recesses and gingival cavity regions of the mold with a liquid denture base material; and
   f) curing the liquid denture base material to form the second portions of the gingival regions of denture base material, and to form a completed denture.

17. The method of claim 14, wherein the forming the labial, buccal, gingival, and flange regions of the denture base, and the posterior and anterior denture teeth are performed by milling denture base material and milling denture tooth material from the block.

18. The method of claim 14, wherein the denture tooth material of the block is non-homogeneous, having a gradient of translucency from lowest translucency to highest translucency along a first axis, and wherein the block is oriented during forming the posterior and anterior denture teeth such that the posterior and anterior denture teeth are formed with lower translucency at bases of the teeth and higher translucency at outer extremities of the teeth.

19. The method of claim 14, wherein the completed denture is defined by a digital three-dimensional model, and wherein the forming the labial, buccal, gingival, and flange regions of the denture, and forming the posterior and anterior denture teeth from the block of denture material are performed based upon data from the three-dimensional model.

20. The method of claim 19, wherein the digital three-dimensional model is based upon three-dimensional data obtained from a digital scan of features of the mouth of a patient to whom the denture is to be fitted.

21. The method of claim 14, wherein the denture is an upper denture further comprised of a palatal region, and the method further comprises forming the palatal region in the completed denture.

* * * * *